United States Patent [19]

Howarth

[11] 4,215,128
[45] Jul. 29, 1980

[54] CLAVULANIC ACID DERIVATIVES THEIR PREPARATION AND USE

[75] Inventor: Thomas T. Howarth, Reigate, England

[73] Assignee: Beecham Group Limited, England

[21] Appl. No.: 942,410

[22] Filed: Sep. 14, 1978

[30] Foreign Application Priority Data

Sep. 20, 1977 [GB] United Kingdom ............... 39040/77
Sep. 21, 1977 [GB] United Kingdom ............... 39251/77
Aug. 25, 1978 [GB] United Kingdom ............... 34593/78

[51] Int. Cl.$^2$ ............................................. C07D 498/04
[52] U.S. Cl. ................................. 424/272; 260/245.3; 542/413; 542/416; 424/114
[58] Field of Search ..................... 260/307 D, 307 FA; 424/272; 542/413, 416

[56] References Cited

FOREIGN PATENT DOCUMENTS 2646000 4/1977 Fed. Rep. of Germany.
2646004 4/1977 Fed. Rep. of Germany.

Primary Examiner—Arthur P. Demers
Attorney, Agent, or Firm—Jacobs & Jacobs

[57] ABSTRACT

This invention provides the compounds of the formula (II):

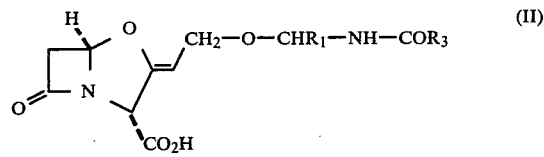

and salts and esters thereof, wherein $R_1$ is H and $R_3$ is H or an aryl, aralkyl, lower alkyl or substituted lower alkyl group or $R_1$ and $R_3$ are joined so that the $CHR_1.NH.CO.R_3$ moiety forms a group of the sub-formula (a):

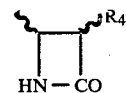

wherein $R_4$ is a hydrogen atom or a $NH.CO.R_5$ group wherein $R_5$ is a lower alkyl, lower alkoxy lower alkyl, aryl, aralkyl, aryloxyalkyl, lower alkoxy or aryloxy group.

The compounds have $\beta$-lactamase inhibitory and antibacterial properties.

The invention also provides a process for their preparation, and pharmaceutical compositions containing them.

78 Claims, No Drawings

CLAVULANIC ACID DERIVATIVES THEIR PREPARATION AND USE

The present invention relates to new ethers of clavulanic acid, to pharmaceutical compositions containing them and to a process for their preparation.

In Belgian Pat. No. 847045, it was disclosed that ethers of clavulanic could be prepared by the reaction of an ester of clavulanic acid with a diazo compound or other etherifying agent. It has now been found that certain novel ethers can be prepared by a facile reaction. This reaction is more suited to industrial application than the process of Belgian Pat. No. 847045 so that the products of this process offer the advantage of greater ease of preparation on the larger scale. In addition compounds of this invention offer a useful range of $\beta$-lactamase inhibitory and anti-bacterial properties and so serve to enhance the spectrum of penicillins and cephalosporins.

The present invention provides the compounds of the formula (I):

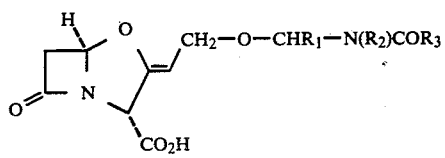

and salts and esters thereof wherein $R_1$ is a hydrogen atom or a lower alkyl, aryl or aralkyl group, $R_2$ and $R_3$ are independently hydrogen, aryl, aralkyl, lower alkyl or substituted lower alkyl, or $R_3$ is joined to $R_1$ to form a 4-, 5- or 6-membered ring or is joined to $R_2$ to form a 5- or 6-membered ring.

When used herein the term "lower" means that the group contains not more than 6 carbon atoms and more suitably not more than 4 carbon atoms.

When used herein the term "aryl" means a phenyl, thienyl or furyl group or a phenyl group substituted by a fluorine or chlorine atom or a lower alkyl or lower alkoxy group.

When used herein the term "aralkyl" means a lower alkyl group substituted by an aryl group.

When used herein the term "substituted alkyl" means a lower alkyl group substituted by a lower alkoxy or aryloxy group.

When used herein the term "aryloxyalkyl" means a lower alkyl group substituted by an O-aryl group.

Suitably the compound of this invention is of the formula (II):

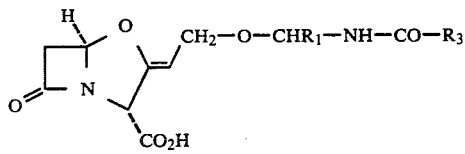

or a salt thereof wherein $R_1$ is a hydrogen atom and $R_3$ is a hydrogen atom or an aryl, aralkyl, lower alkyl or substituted lower alkyl group or $R_1$ and $R_3$ are joined so that the CHR$_1$NH.CO.R$_3$ moiety forms a group of the subformula (a):

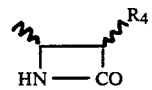

wherein $R_4$ is a hydrogen atom or a NH.CO.R$_5$ group wherein $R_5$ is a lower alkyl, lower alkoxy lower alkyl, aryl, aralkyl or aryloxyalkyl group. $R_5$ may also be lower alkoxy or aryloxy.

One suitable sub-group of compounds of the formula (II) are those of the formula (III):

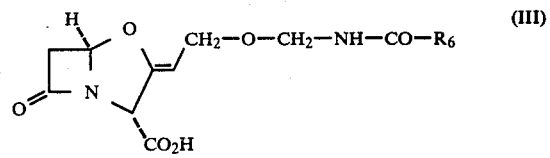

and salts and esters thereof wherein $R_6$ is a hydrogen atom or an aryl, aralkyl, lower alkyl or substituted lower alkyl group.

Suitably $R_6$ is a hydrogen atom; an alkyl group of up to 4 carbon atoms; an alkyl group of up to 4 carbon atoms substituted by an alkoxy group of up to 4 carbon atoms; a phenyl group; a phenyl group substituted by a fluorine or chlorine atom or a methyl or methoxyl group; a benzyl group; or a benzyl group substituted by a fluorine or chlorine atom or a methyl or methoxyl group.

Favoured values for $R_6$ include the methyl group, the ethyl group and the phenyl group.

A further suitable sub-group of compounds of the formula (II) are those of the formula (IV)

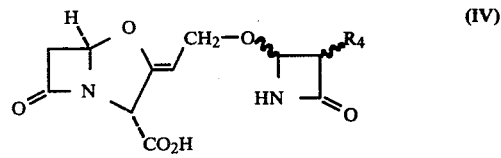

and salts and esters thereof wherein $R_4$ is as defined in relation to sub-formula (a).

Suitably $R_4$ is a hydrogen atom.

Suitably $R_4$ is a NH.CO.R$_7$ group where $R_7$ is an alkyl group of up to 4 carbon atoms; an alkyl group of up to 4 carbon atoms substituted by an alkoxy group of up to 4 carbon atoms; an aryl group; an aralkyl group; or an aryloxyalkyl group. Similarly $R_7$ may be an alkoxy group of up to 4 carbon atoms or an aryloxy group.

Favoured values for $R_7$ include the methyl, ethyl, phenyl, benzyl, phenoxymethyl, p-methoxyphenyl, p-methoxyphenoxymethyl, ethoxyethyl and like groups.

Particularly suitable values for $R_7$ include the phenoxymethyl and benzyl groups.

A further suitable sub-group of compounds of the formula (I) is that of the formula (V):

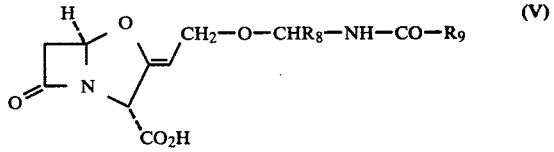

and salts and esters thereof wherein $R_8$ is a lower alkyl, aryl or aralkyl group and $R_9$ is a hydrogen atom or an aryl, aralkyl, lower alkyl or substituted lower alkyl group.

Suitable values for $R_8$ include methyl, ethyl, n-propyl, n-butyl and phenyl. A favoured value for $R_8$ is the methyl group.

Suitably $R_9$ is a hydrogen atom; an alkyl group of up to 4 carbon atoms; an alkyl group of up to 4 carbon atoms substituted by an alkoxy group of up to 4 carbon atoms; a phenyl group; a phenyl group substituted by a fluorine or chlorine atom or a methyl or methoxyl group; a benzyl group; or a benzyl group substituted by a fluorine or chlorine atom or a methyl or methoxyl group.

Favoured values for $R_9$ include the methyl group, the ethyl group and the phenyl group.

Another suitable sub-group of compounds of the formula (I) is that of the formula (VI):

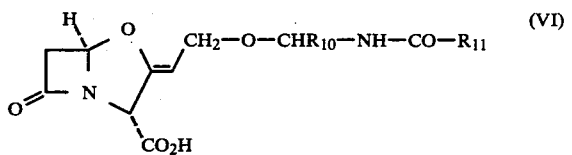

(VI)

and salts and esters thereof wherein $R_{10}$ is a hydrogen atom or a lower alkyl group and $R_{11}$ is a lower alkyl group substituted by an amino group and optionally by an aryl group or $R_{10}$ and $R_{11}$ are joined so that the $CHR_{10}$—NH—CO—$R_{11}$ moiety forms a group of the sub-formula (b):

(b)

Suitably $R_{10}$ is a hydrogen atom. Suitably $R_{10}$ is a methyl, ethyl, n-propyl or n-butyl group of which methyl and ethyl are preferred.

One suitable sub-group of compounds of the formula (VI) is that of the formula (VII):

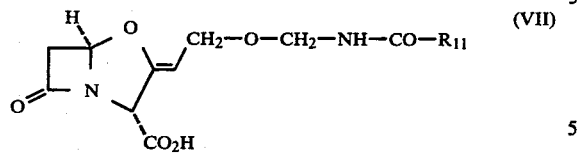

(VII)

and salts and esters thereof wherein $R_{11}$ is an alkyl group of up to 4 carbon atoms substituted by an amino group or $R_{11}$ is an alkyl group of up to 4 carbon atoms substituted by an amino group and by an aryl group.

Favoured values for $R_{11}$ include those groups wherein the amino substituent is on the α-carbon atom, for example the aminomethyl, α-aminoethyl, α-aminobenzyl and like groups.

A further suitable sub-group of compounds of the formula (VI) are the compound of the formula (VIII):

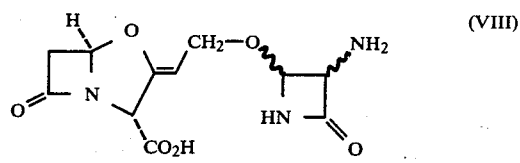

(VIII)

and salts and esters thereof. The compound of the formula (VIII) may have the cis- or trans-stereochemistry about the monocyclic β-lactam or may be in the form of mixtures of such compounds.

Another suitable sub-group of compounds of the formula (I) are those of the formula (IX):

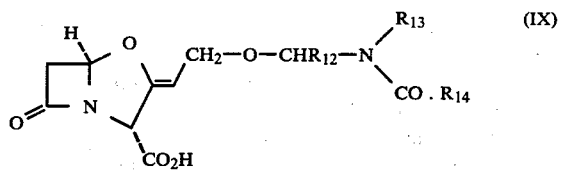

(IX)

and salts and esters thereof wherein $R_{12}$ is a hydrogen atom or a lower alkyl, aryl or aralkyl group, $R_{13}$ is an aryl, aralkyl, lower alkyl or substituted lower alkyl group and $R_{14}$ is a lower alkyl group or is joined to $R_{12}$ to form a 4-, 5- or 6-membered ring or is joined to $R_{13}$ to form a 5- or 6-membered ring.

Suitable acyclic values for $R_{12}$ include the hydrogen atom and the methyl, ethyl, n-propyl, n-butyl and phenyl groups. The hydrogen atom is a particularly suitable acyclic value for $R_{12}$, as is the methyl group.

Suitable acyclic values for $R_{13}$ include an alkyl group of up to 4 carbon atoms; an alkyl group of up to 4 carbon atoms substituted by an alkoxy group of up to 4 carbon atoms; a phenyl group; a phenyl group substituted by a fluorine or chlorine atom or a methyl or methoxyl group; a benzyl group; or a benzyl group substituted by a fluorine or chlorine atom or a methyl or methoxyl group.

Favoured acyclic values for $R_{13}$ include the methyl group, the ethyl group and the phenyl group and the optionally salted or esterified carboxymethyl group.

Suitable values for —$CHR_{12}$—$N(R_{13})COR_{14}$ when $R_{12}$ and $R_{14}$ are linked include those of the sub-formula (c):

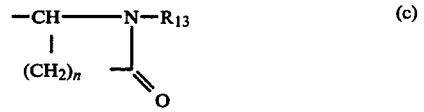

(c)

wherein n is 1, 2 or 3 and $R_{13}$ is an acyclic moiety as defined in relation to formula (VII).

Suitable values for —$CHR_{12}$—N—($R_{13}$)$COR_{14}$ when $R_{13}$ and $R_{14}$ are linked include those of the sub-formula (d):

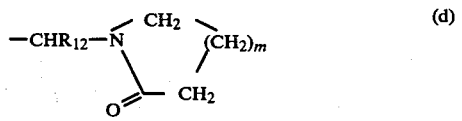

(d)

wherein m is 1 or 2 and $R_{12}$ is an acyclic moiety as defined in relation to formula (IX).

Favourably in relation to sub-formula (c) n is 1 and $R_{13}$ is an optionally salted or esterified carboxymethyl group.

Favourably in relation to sub-formula (d) $R_{12}$ is a hydrogen atom.

A preferred aspect of this invention is provided by the compound of the formula (X):

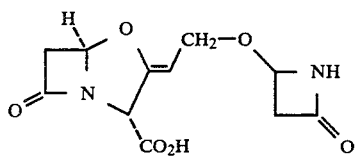
(X)

and salts and esters thereof. Salts of the compound of the formula (X) have been found to produce good blood levels of the β-lactamase inhibitor after administration by oral or parenteral routes. Thus it will be realised that the pharmaceutically acceptable salts of the compound of the formula (X) are an especially preferred aspect of this invention.

Further favoured aspects of this invention are provided by the compounds of the formulae (XI)–(XIV):

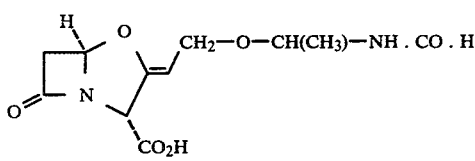
(XI)

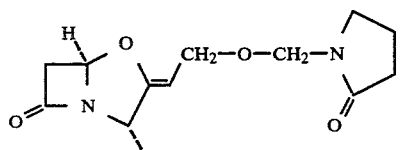
(XII)

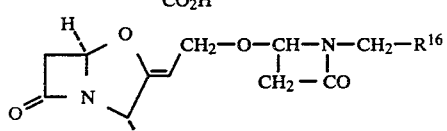
(XIII)

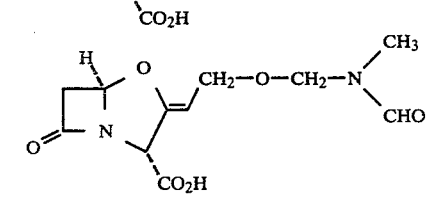
(XIV)

and salts and esters thereof wherein $R^{16}$ is H or $CO_2H$.

The compounds of the formula (I) are aptly presented as the free acid per se or as a salt thereof.

Suitably the compounds of the formula (I) are presented as the free acid but more favourably the compounds of the formula (I) are in the form of a salt. Apt salts include alkali or alkaline earth metal salts such as the lithium, sodium, potassium, calcium or magnesium salts. Other apt salts include the ammonium salt and salts of amines such as lower alkylamine salts such as methylamine, ethylamine, dimethylamine or the like salts or salts of cyclic bases such as pyrrolidine or quarternary ammonium salts such as the tetramethyl ammonium salt.

Particularly suitable salts include the lithium, sodium, potassium, calcium and magnesium salts.

A preferred salt is the sodium salt. Another preferred salt is the potassium salt. A further preferred salt is the lithium salt. An additional preferred salt is the magnesium salt. An alternative preferred salt is the t-butylamine [$(CH_3)_3CNH_2$] salt.

The preceding salts are also favoured in relation to the compounds of the formulae (II), (III) and (VII)–(XII).

An exception to the preceding rule occurs when the compound of the formula (I) contains an amino group. In this circumstance the compound of the formula (I) is most suitably zwitterionic.

Suitable esters of the compounds of the formulae (I)–(XII) include those of the sub-formulae (e) and (f):

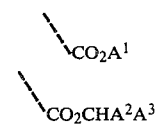

wherein $A^1$ is an alkyl group of 1–6 carbon atoms optionally substituted by an alkoxyl or acyloxy group of 1–7 carbon atoms; $A^2$ is an alkenyl group of up to 5 carbon atoms or is a phenyl group optionally substituted by a fluorine, chlorine, bromine, nitro or alkyl or alkoxyl of up to 4 carbon atoms; and $A^3$ is a hydrogen atom, an alkyl group of up to 4 carbon atoms or a phenyl group optionally substituted by a fluorine, chlorine, bromine, nitro or alkyl or alkoxyl of up to 4 carbon atoms.

Certain favoured groups $A^1$ include the methyl, ethyl, methoxymethyl, acetoxymethyl, acetoxyethyl, phthalidyl, ethoxycarbonyloxymethyl, α-ethoxycarbonyloxyethyl, pivaloyloxymethyl and the like groups.

Certain favoured groups $A^2$ include the phenyl, methoxyphenyl and nitrophenyl groups. A particularly favoured moiety $A^3$ is the hydrogen atom.

The salts of the compounds of the formulae (I)–(XIV) are envisaged primarily as pharmaceutical agents although they may also be employed as intermediates, for example in preparing other salts or in the preparation of the parent acid or in the preparation of esters. The compounds of the formulae (I)–(XIV) are envisaged primarily as intermediates in the preparation of the nontoxic salts but may also be employed as pharmaceutical agents.

The compounds of the invention in which the side chain carbon atom between the oxygen and nitrogen atoms is substituted by other than hydrogen may be in the R— or S—forms although for convenience of preparation the R,S—mixture is advantageous.

The present invention also provides a pharmaceutical composition which comprises a compound of this invention and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics such as β-lactam containing antibiotics. Such compositions may be formulated in known manner, for example by mixing. Favourably such formulations are manufactured in a dry environment and are formulated from dry ingredients.

Injectable or infusable compositions of salts of a compound of the formula (I) are particularly suitable as high blood levels of a compound of the formula (I) can occur after administration by injection or infusion. Thus, one preferred composition aspect of this invention comprises an injectable salt of a compound of the formula (I) in sterile form, for example the sterile sodium or potassium salt. Most suitably the composition is in unit dosage form. of the formula (I) or a salt or ester thereof adapted for oral administration form a further preferred composition aspect of this invention.

Compositions of this invention preferably comprise a non-toxic salt of a compound of the invention, for example a sodium or potassium salt or a salt with a non-tox amine. A preferred salt for this use is the sodium salt. Another preferred salt for this use is the potassium salt.

The compound of the formula (I) or its salt or ester may be present in the composition as sole therapeutic agent or it may be present together with other therapeutic agents such as a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, cephalothin, cefazolin, cephalexin, cephacetrile, cephamondole nafate, cephapirin, cephradine, 4-hdroxycephalexin, cefaparole, cephaloglycine, and other well known penicillins and cephalosporins or pro-drugs therefor such as hetacillin, metampicillin, 4-acetoxyampicillin, the acetoxymethyl, α-ethoxycarbonyloxyethyl, pivaloyloxymethyl or phthalidyl esters of ampicillin or amoxycillin or the phenyl, tolyl or indanyl esters of carbenicillin or ticarcillin or the like. Such compounds are frequently used in the form of a hydrate and/or salt such as a sodium or potassium salt of a carboxyl group, or hydrochloride of amine functions and the like.

Naturally if the penicillin or cephalosporin present in the composition is not suitable for oral administration then the composition will be adapted for parenteral administration.

When present together with a cephalosporin or penicillin, the ratio of a compound of the formula (I) or its salt or ester present to the other antibacterial agent may vary over a wide range of ratios, for example 3:1 to 1:10 and advantageously may be from 1:1 to 1:8, for example, 1:2, 1:3, 1:4, 1:5 or 1:6.

The total quantity of compound of the formula (I) in any unit dosage form will normally be between 25 and 1000 mg and will usually be between 50 and 500 mg for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administrated each day of treatment but more usually between 100 and 750 mg of the compounds of the invention will be administered per day, for example as 1–6 doses, more usually 2–4 doses, for example as 3 doses.

The penicillin or cephalosporin in synergistic compositions of this invention will normally be present at approximately the amount at which it is conventionally used.

Particularly favoured compositions of this invention will contain from 150–1000 mg of amoxycillin, ampicillin or a pro-drug therefor and from 25–500 mg of a compound of the formulae (I)–(XIV) or a salt or ester thereof and more suitably from 200–750 mg of amoxycillin or a salt thereof and from 50–250 mg of a salt of a compound of the formulae (I)–(XIV).

Most suitably a pharmaceutically acceptable salt of the compound of the formula (X) is used.

Most suitably this form of the composition will comprise ampicillin or its salt or amoxycillin or its salt. The ampicillin is suitably present as ampicillin anhydrate, ampicillin trihydrate or sodium ampicillin. The amoxycillin is suitably present as amoxycillin trihydrate or sodium amoxycillin. The orally administrable compositions will normally comprise the zwitterion and the injectable composition will normally comprise the sodium salt.

The weights of the antibiotics in such compositions are expressed on the basis of antibiotic per se theoretically available from the composition.

The compositions of this invention may be used to treat infections caused by strains of gram-positive and gram-negative bacteria such as *Staphylococcus aureus, Escherichia coli, Klebsiella aerogenes, Haemophilus influenzae, Neisseria, gonhorrea, Proteus mirabilis, Proteus vulgaris, Pseudomonas aeruginosa, Bacteroides fragilis* and the like including many penicillinase producing strains.

The compositions of this invention may be administered so that the therapeutic effect is achieved without any clear signs of acute toxicity being seen.

The compositions of this invention benefit from formulation under dry conditions.

The present invention provides a process for the preparation of compounds of the formula (I) or a salt or ester thereof, which comprises the reaction of an ester of clavulanic acid with a compound of the formula (XV):

$$Y-CHR_1-NR_2-CO-R_3 \qquad (XV)$$

wherein $R_1$, $R_2$ and $R_3$ are as defined in relation to formula (I) and Y is a displaceable group; and thereafter, if desired, converting the thus produced ester into the free acid or a salt thereof.

Suitable moieties Y include conventional displaceable groups such as carboxylate esters such as $O.CO.R^{15}$ or $O.CO.OR^{15}$ where $R^{15}$ is an inert organic group such as a lower alkyl group (such as a methyl, ethyl, propyl or butyl group), a phenyl, benzyl, methoxyphenyl, methylphenyl, halophenyl, nitrophenyl or like group; or a O.CO.H group; or other moiety displaceable by a nucleophile such as a halogen atom, for example chlorine or bromine atom; or a hydroxyl group.

Generally the process of this invention will take place in the presence of a catalyst such as zinc diacetate or its chemical equivalent when Y is a carboxylate ester or in the presence of a non-nucleophilic base and/or silver oxide and/or a soluble silver salt when Y is a halogen atom or in the presence of a Lewis acid such as borontrifluoride (for example as the etherate) or dehydrating agent such as p-toluene sulphonic acid when Y is a hydroxyl group.

Naturally any amino group optionally present in the compound of formula (XV) will be protected during the etherification and the protecting group removed thereafter.

The etherification may be carried out at a non-extreme depressed, ambient or elevated temperature such as −10° to 120° C.; for example the temperature of the reaction may be slightly or moderately elevated (for example 30° to 100° C.) when employing zinc acetate as a catalyst or depressed (for example 0° to 15° C.) when BF$_3$ is used as a catalyst.

The etherification reaction is generally carried out in an inert non-hydroxylic medium such as a hydrocarbon, halohydrocarbon or ester solvent, for example benzene, toluene, methylene chloride, ethyl acetate, chloroform, or mixtures thereof.

After the reaction is complete, the desired ester can be obtained by evaporation of the solvent and purification of the product chromatographically for example by gradient elution using solvent mixtures such as ethyl acetate/cyclohexane or ethyl acetate/petroleum ether (60°–80°) using silica gel or the like as stationary phase.

In a further aspect the present invention also provides a process for the preparation of compound of the formula (I) or a salt thereof which comprises the de-esterification of an ester of the compound of the formula (I) optionally in the presence of a base.

Such de-esterification may involve hydrolysis or hydrogenolysis. Thus for example an ester such as a methyl, ethyl, methoxymethyl, ethoxymethyl, acetoxymethyl or like ester may be subjected to mild base hydrolysis to yield a salt of a compound the formula (I). Suitably these esters may be hydrolysed by maintaining the pH of the medium at 7.5 to 9 until the hydrolysis is effected. Most suitably a readily hydrolysable ester such as the methoxymethyl ester is employed in this process. The pH may be maintained in the desired range in a pH-stat by the addition of a solution or suspension of a base such as LiOH, NaOH, KOH, Ca(OH)$_2$, Mg(OH)$_2$, NaHCO$_3$, Na$_2$CO$_3$, MgCO$_3$ or the like at a rate that prevents the accumulation of excess base which would cause the pH to increase unacceptably.

Suitable methods of hydrogenolysis of esters of the compounds of formula (I) include hydrogenation in the presence of a transition metal catalyst. Suitable hydrogenolysable esters of the compound of the formula (I) include those where the ester moiety is of the sub-formula CO$_2$CHA$^2$A$^3$ as hereinbefore defined and of these the benzyl and p-methoxybenzyl esters are particularly suitable. The p-nitrobenzyl ester is also apt.

The pressure of hydrogen used in the reaction may be low, medium or high but in general an approximately atmospheric or slightly superatmospheric pressure of hydrogen is preferred. The transition metal catalyst employed is preferably palladium, for example palladium on charcoal, palladium on barium sulphate, palladium on calcium carbonate or the like. The hydrogenation may be effected in any convenient solvent in which the ester is soluble such as tetrahydrofuran, ethyl acetate, ethanol, aqueous ethanol or the like. If this hydrogenation is carried out in the presence of a base then a salt of the compounds of formula (I) is produced. Suitable bases for inclusion include NaHCO$_3$, Na$_2$CO$_3$, K$_2$CO$_3$, CaCO$_3$, MgCO$_3$, LiHCO$_3$, N(C$_2$H$_5$)$_3$.HO$_2$C.CH$_3$ and the like. If no base is present then hydrogenation leads to the preparation of an acid of formula (I) which may then be neutralised if desired to yield a salt. Suitable bases for such neutralisation include LiOH, NaHCO$_3$, KOH, Ca(OH)$_2$, Ba(OH)$_2$, Mg(OH)$_2$, NH$_4$OH, N(C$_2$H$_5$)$_3$, N(C$_2$H$_5$)$_3$.HO$_2$CCH$_3$, Na ethylhexanoate, K ethylhexanoate and the like e.g. MgO and NH$_2$C(CH$_3$)$_3$.

The lithium salts of the compounds of formula (I) tend to be more easily prepared in pure crystalline from than other salts of the compounds of formula (I). It is therefore often convenient to first form the lithium salt and then convert this into a further salt by ion-exchange, for example by passing a solution of the lithium salt through a bed of a cation exchange resin in sodium, potassium, calcium, ammonium or like form. Suitable cation exchange resins include Amberlite IR 120 and equivalent resins. Another salt suitable for use as an intermediate in this way is the t-butylamine salt.

The zwitterions of the formulae (VI) to (VIII) are normally formed by a simultaneous de-esterification and de-protection reaction. A de-esterification/de-protection reaction convenient for laboratory use comprises the catalytic hydrogenation of a compound containing benzyloxycarbonylamino group and a benzyl ester. This reaction preferably uses a palladium catalyst such as palladium on charcoal and may employ a low, ambient or high pressure of hydrogen. The hydrogenation is generally carried out in an organic solvent at a non-extreme temperature, for example in aqueous tetrahydrofuran at ambient temperature.

Other amine protecting groups which may be employed include the azido group, the protonated amino group, enamine protected forms and the like. These may also be removed by mild processes such as reduction of an azide, hydrolysis of an enamine (such as that derived from a β-ketoacid ester such as ethylacetoacetate) or the like method.

Crystalline salts of the compounds of the formula (I) may be solvated, for example hydrated.

The salts (for example the sodium salt) of the compounds of formula (I) may be converted into the corresponding esters in conventional manner, for example by reaction with a reactive halide in solution in dimethylformamide or like solvent. Esters may similarly be prepared by the reaction in an inert solvent of a compound of formula (I) with a diazocompound or with an alcohol in the presence of a condensation promoting agent such as dicyclohexylcarbodiimide. Other reagents for use in this manner include triethyloxonium tetrafluoroborate or the like. Suitable reactive halides for use in the above process include phthalidyl bromide, pivoloyloxymethyl bromide, benzyl bromide, methyl iodide and the like. Amino functions will normally be protected during the reaction.

A favoured process of this invention comprises the reaction of an ester of clavulanic acid with a compound of the formula (XVIII):

(XVIII)

wherein R$_4$ is as defined in relation to formula (I) and Y$^1$ is a group of the formula O.CO.R$^{15}$ wherein R$^{15}$ is as defined in relation to formula (XV); and thereafter if desired converting the initially produced ester of the compound of the formula (IV) to the acid of the formula (IV) or its salt.

Most suitably in this process R$^{15}$ is a lower alkyl, aryl or aralkyl group.

Preferably in this process $Y^1$ is an acetoxy group.
Preferably in this process $R_4$ is hydrogen.

This process may be brought about using the general reaction conditions hereinbefore described.

Yet another favoured process of this invention comprises the hydrolysis or hydrogenolysis of a hydrolysable or hydrogenolysable ester of a compound of the formula (X) to yield the acid of the formula (X) or a salt thereof. The present invention also provides the compounds of the formula (XIX):

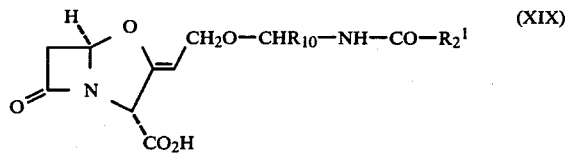

and salts and esters thereof wherein $R_{10}$ is as defined in relation to formula (VI) and $R_2$ is a group $R_{11}$ as defined in relation to formula (VI) in which the amino group is protected. These compounds are useful as intermediates.

For the preparation of compounds of the formula (XIV), it is often convenient to generate the appropriate compound of the formula (XV) by electrolysis of dimethylformamide in the presence of an ester of clavulanic acid. An inert electrolyte, such as $LiBF_4$ or $LiClO_4$, will be present during the electrolysis.

Suitably, the electrolysis is conducted by passing a current of 200–300 mA between a pair of platinum foil electrodes placed 1–5 mm apart. Optionally an inert diluent such as nitromethane may be present. The reaction temperature is maintained around 30°–20° C. by applying external cooling.

Analogous compounds of the formula (XV) may similarly be generated by electrolysis of a compound of the formula $R_1CH_2N(R_2)COR_3$.

The esters of the compounds of the formula (XIX) are particularly suitable intermediates and especially those which are cleavable by hydrogenolysis, for example the benzyl and substituted benzyl esters. Those compounds of the formula (XIX) wherein the protected amino group is a benzyloxycarbonylamino group are also particularly suitable intermediates. The compounds of the formula (XIX) containing both these features are preferred.

The following Examples illustrate the inventions. (The $OCHR_1N(R_2)COR_3$ side chains [see formula (I)] illustrated in the Examples are particularly apt).

EXAMPLE 1

Benzyl 9-O-(azetidin-2'-on-4'-yl)clavulanate

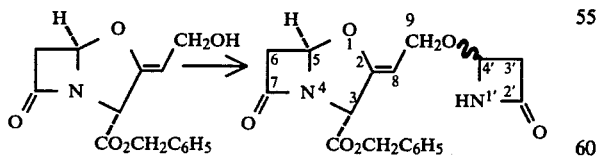

Benzyl clavulanate (5.78 g; 0.02 mole) (±)-4-acetoxyazetidin-2-one (1.29 g; 0.01 mole) and zinc acetate dihydrate (0.218 g; 0.001 mole) were heated under reflux in benzene (50 ml) for 1.5 hours. The suspension was filtered and the filtrate concentrated to low volume in vacuo. The residue was fractionated on silica gel eluting with ethyl acetate-cyclohexane (1:1) to give the viscous, oily product (2.42 g) as a mixture of two diastereoisomers; $v_{max}$ ($CHCl_3$), 1805, 1750–1775 (broad), and 1695 $cm^{-1}$; n.m.r.$\delta$ ($CDCl_3$) 2.91 (2H, m, 3'-$C\underline{H}_2$), 3.06 (1H, d, J 16.5 Hz, 6$\beta$-$C\underline{H}$), 3.53 (1H, dd, J 16.5 and 2.5 Hz, 6$\alpha$-$C\underline{H}$), 4.16 (2H, d, J 7.5 Hz, =CH-$C\underline{H}_2$-), 4.83 (1H, br.t., J 7.5 Hz, =$C\underline{H}$-), 5.02 (1H, m, 4'-$C\underline{H}$), 5.18 (1H, br.s, 3-$C\underline{H}$), 5.23 (2H, s, -$CO_2C\underline{H}_2$), 5.73 (1H, d, J 2.5 Hz, 5-$C\underline{H}$), 7.08 (1H, br., $N\underline{H}$), 7.40 ppm (5H, s, $C_6\underline{H}_5$).

EXAMPLE 2

Sodium 9-O-(azetidin-2'-on-4'-yl)clavulanate

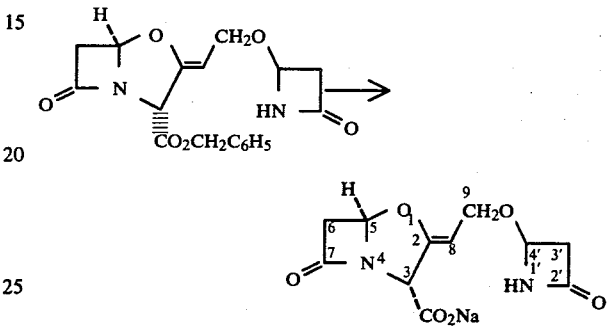

Benzyl 9-O-(azetidin-2'-on-4'-yl)clavulanate (0.84 g) in tetrahydrofuran (20 ml) was hydrogenated over 10% Pd/C (0.28 g) at ambient temperature and pressure for 15 minutes. After this time, debenzylation was shown (tlc) to be complete. The catalyst was filtered and the filtrate concentrated in vacuo to leave a clear, viscous oil which was 9-O-(azetidin-2'-on-4'-yl)-clavulanic acid. Treatment of this oil with sodium hydrogen carbonate (186 mg; 0.95 equivalents) in water (10 ml) gave an aqueous solution of the diastereomeric mixture of sodium salts. Evaporation of the water in vacuo gave an oil. Trituration with ethanol and re-evaporation of the solvent in vacuo was carried out several times to give a semi-solid residue. Trituration with ether then gave a white solid (610 mg) which was shown, from the following spectroscopic properties to be the required product; $v_{max}$ (KBr) 1750–1790, 1695 and 1620 $cm^{-1}$ $\delta(D_2O)$; ($CH_3CN$ internal standard at $\delta=2.00$ ppm) 2.72 (1H, d, J 16 Hz, 3'-$C\underline{H}$), 3.03 (1H, d, J 17.5 Hz, 6$\beta$-$C\underline{H}$), 3.12 (1H, dd, J 3.5 and 16 Hz, 3'-$C\underline{H}$), 3.52 (1H, dd, J 17.5 and 2.5 Hz, 6$\alpha$-$C\underline{H}$), 4.16 (2H, d, J 7.5 Hz, 9-$C\underline{H}_2$), 4.85 (1H, br.t., J 7.5 Hz, 8-$C\underline{H}$), 4.92 (1H, br.s., 3-$C\underline{H}$), 5.15 (1H, d, J 3.5 Hz, 4'-$C\underline{H}$), 5.68 (1H, d, J 2.5 Hz, 5-$C\underline{H}$).

EXAMPLE 3

Benzyl 9-O[3'-(S)-phenoxyacetamido-2'-oxoazetidin-4'-(S)-yl]clavulanate and Benzyl 9-O[3'-(S)-phenoxyacetamido-2'-oxoazetidin-4'-(R)-yl]clavulanate

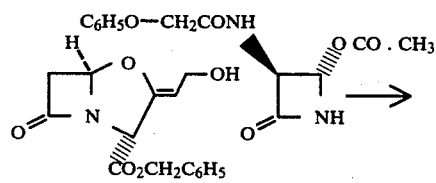

-continued

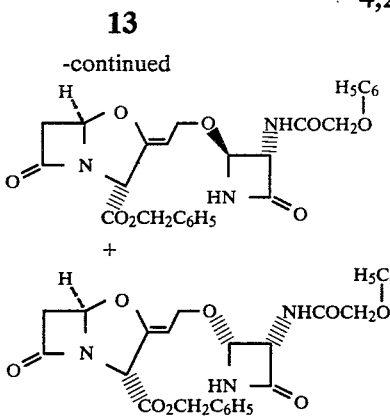

A solution of benzyl clavulanate (1.734 gm) and 4-acetoxy-3-phenoxyacetamido-azetidin-2-one (1.112 gm) in benzene (15 ml) was treated with zinc acetate (87 mgs) and refluxed using a Dean and Stark water separator for 1½ hours. The mixture was then cooled and the solvent removed under vacuum. The products were separated by column chromatography using gradient elution (Kieselgel, 1:1 ethyl acetate:cyclohexane going to 2:1 ethyl acetate:cyclohexane). Excess benzyl clavulanate was first eluted followed by benzyl 9-O[3'-(S)-phenoxyacetamido-2'-oxoazetidin-4'(S)-yl]-clavulanate (557 mgs), m.p. 127°-128° C. (from ethyl acetate-cyclohexane).

I.R. $\nu_{max}$ (nujol) 3270, 1795, 1775, 1755, 1693 and 1665 cm$^{-1}$. N.M.R. $\delta$(CDCl$_3$) 3.02 (1H, d, J=17 Hz), 3.41 (1H, dd, J=3 and 17 Hz), 4.16 (2H, d, J=7 Hz), 4.44 (2H, s), 4.5–4.9 (2H, m), 5.06 (2H, broad s), 5.15 (2H, s), 5.63 (1H, d, J=3 Hz), 6.2–7.5 (2H, very broad, exchangeable), 6.75–7.55 (10H, m). Analysis. Found: C, 61.73; H, 5.18; N, 8.24: C$_{26}$H$_{25}$N$_3$O$_8$ requires: C, 61.53; H, 4.97; N 8.24.

Further elution gave benzyl 9-O[3'-(S)-phenoxyacetamido-2'-oxoazetidin-4'-(R)-yl]-clavulanate [520 mgs; M.p. 82°-85° (from ethyl acetate-cyclohexane)].

I.R. $\nu_{max}$ (nujol) 3280, 3170, 1802, 1780, 1755, 1692 and 1658 cm$^{-1}$. N.M.R. $\delta$(CDCl$_3$) 2.98 (1H, d, J=17 H), 3.39 (1H, dd, J=3 and 17 Hz) 4.07 (2H, d, J=7 Hz), 4.45 (2H, s), 4.67 (1H, broad t, J=7 Hz), 4.95–5.06 (2H, m), 5.11 (2H, s) 5.35 (1 H, complex d, J=9 Hz), 5.59 (1H, d, J=3 Hz), 6.7–7.7 (12H, m,). Analysis. Found; C, 61.72; H, 5.17; N, 8.02; C$_{26}$H$_{25}$N$_3$O$_8$ requires; C, 61.53; H, 4.97; N, 8.24: (The products were obtained from solution in the elution solvent by evaporation of the solvent under reduced pressure).

EXAMPLE 4

Benzyl 9-O(N-benzoylaminomethyl)clavulanate

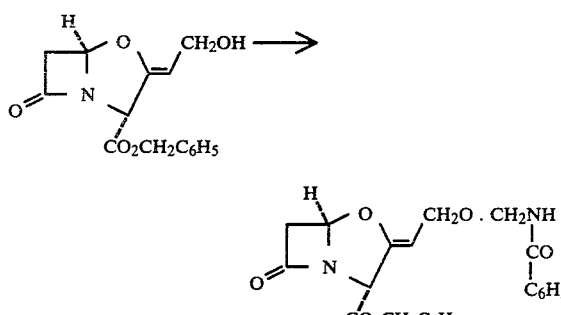

Benzyl clavulanate (234 mg) in methylene chloride (6 ml) was treated with N-hydroxymethylbenzamide (122 mg) in ethyl acetate (6 ml) and cooled to 0°. To the magnetically stirred solution was added a crystal of p-toluenesulphonic acid and the solution was allowed to warm to room temperature. After 1 hour, a further 244 mg of N-hydroxymethylbenzamide was added and the solution stirred overnight at room temperature. The resulting suspension was filtered and the filtrate concentrated in vacuo. The residue was fractionated on silica gel eluting with ethyl acetate-hexane (1:1) to give the title product after evaporation of the solvent as a viscous oil (105 mg); i.r. (chloroform) 1805, 1750, 1695 and 1665 cm$^{-1}$, n.m.r. $\delta$(CDCl$_3$), 2.93 (1H, d, J 17.5 Hz, 6$\beta$-C$\underline{H}$), 3.41 (1H, dd, J 17.5 and 2.5 Hz, 6$\alpha$-C$\underline{H}$), 4.20 (2H, d, J 7.5 Hz, 9-C$\underline{H}_2$), 4.85 (1H, t, J 7.5 Hz, 8-C$\underline{H}$), 4.90 (2H, d, J 7 Hz, O-C$\underline{H}_2$NH), 5.10 (1H, bs, 3-C$\underline{H}$), 5.17 (2H, s, OC$\underline{H}_2$C$_6$H$_5$), 5.72 (1H d, J 2.5 Hz, 5-C$\underline{H}$), 7–8.1 ppm (11H, m, 2×C$_6$H$_5$, N$\underline{H}$).

EXAMPLE 5

Benzyl 9-O(N-benzoylaminomethyl)clavulanate

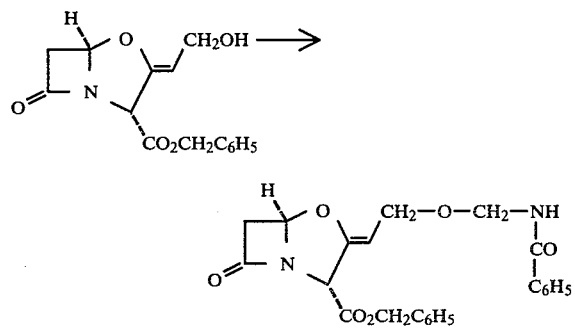

Benzyl clavulanate (273 mg) in ethyl acetate (10 ml) was treated with N-hydroxymethylbenzamide (286 mg) followed by boron trifluoride etherate (5 drops) at room temperature. After 1 hour, the solution was washed with dilute aqueous sodium hydrogen carbonate, water and then dried (MgSO$_4$). The organic layer was evaporated and the residue fractionated on silica gel, as in Example 4 to yield benzyl 9-O-(N-benzoylaminomethyl)clavulanate (46 mg).

EXAMPLE 6

Benzyl 9-O-(N-benzoylaminomethyl)clavulanate

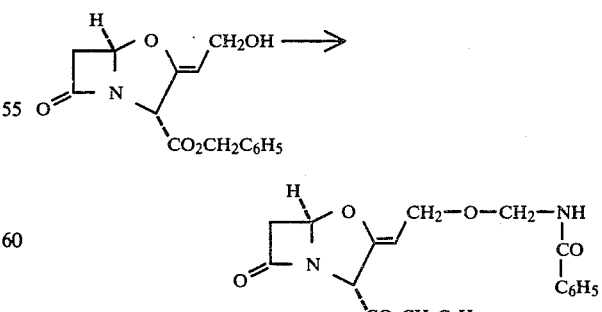

Benzyl clavulanate (1.45 g), N-acetoxymethylbenzamide (0.97 g) and powered zinc acetate dihydrate (109 mg) were heated under reflux in toluene (65 ml; sodium dried) for 4 hours. The cooled supernatant liquid was decanted and evaporated in vacuo. Fractionation of the residue on silica gel, as in Example 4, gave the title product (335 mg).

The N-acetoxymethylbenzamide was obtained as follows: N-hydroxymethylbenzamide (5 g) was heated at 80° C. for 1 hour in glacial acetic acid (50 ml). The cooled solution was evaporated in vacuo and the residue was partitioned between water (50 ml) and ethyl acetate (50 ml). The organic layer was washed with dilute aqueous sodium hydrogen carbonate and water and then dried (MgSO₄). Evaporation of the solvent in vacuo gave an oil which was fractionated on silica gel eluting with ethyl acetate-hexane (1:1) to give an oil (3.52 g) which eventually solidified.

N.m.r. δ(CDCl₃) 2.03

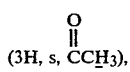

(3H, s, CC$\underline{H}$₃), 5.58 (2H, d, 7 Hz, C$\underline{H}$₂NH), 7.3–8.1 (6H, m, C₆$\underline{H}$₅, N$\underline{H}$).

EXAMPLE 7

Sodium 9-O-(N-benzoylaminomethyl)clavulanate

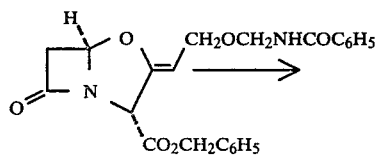

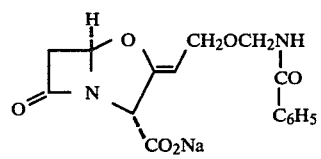

Benzyl 9-O-(N-benzoylaminomethyl)clavulanate (300 mg) in tetrahydrofuran (10 ml) was hydrogenated over 10% Pd/C (100 mg) at ambient temperature and pressure for 10 minutes. The catalyst was filtered and the filtrate was concentrated to low volume in vacuo. The oily residue was treated with sodium hydrogen carbonate (58 mg) in water (3 ml) and the resulting solution was extracted with ethyl acetate (1 ml). The aqueous solution was evaporated in vacuo and the residual oil triturated several times with acetone - ether until a semi-solid was obtained. Trituration with ethyl acetate then gave a cream solid which was filtered off and dried under reduced pressure in a desiccator to yield sodium 9-O-(N-benzoylaminomethyl)clavulanate (191 mg) as a solid.

I.r. (KBr) 1780, 1695, 1610–1660 cm⁻¹.

N.m.r. δ(D₂O) 2.91 (1H, d, J 18 Hz, 6β-C$\underline{H}$), 3.48 (1H, dd, J 18 Hz and 2.5 Hz, 6α-C$\underline{H}$), 4.18 (2H, d, J 7.5 Hz, 9-C$\underline{H}$₂), 4.84 (2H, s, OC$\underline{H}$₂N), 4.90 (1H, s, 3-C$\underline{H}$), 5.72 (1H, d, J 2.5 Hz, 5-C$\underline{H}$), 7.4–7.9 (5H, m, C₆$\underline{H}$₅).

EXAMPLE 8

Benzyl 9-O-(1-formamidoethyl)clavulanate

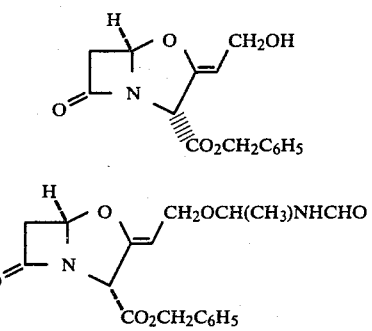

N-(1-Acetoxyethyl)formamide (520 mg., 4 mmole) and benzyl clavulanate (1.2 g, 4.15 mmole) were dissolved in dry benzene (30 ml). Finely powdered zinc acetate dihydrate (400 mg, 1.8 mmole) was added to the solution, and the mixture was stirred and refluxed with azeotropic removal of water for 4 hours. The mixture was cooled, diluted with ethyl acetate (100 ml) and filtered. The filtrate was washed with saturated sodium bicarbonate solution (50 ml), water (50 ml), and saturated brine (50 ml). The solution was dried (sodium sulphate) and the solvent was evaporated under reduced pressure to yield a yellow gum. The gum was chromatographed on silica gel (25 g) using 1:3 - 3:2 ethyl acetate/petroleum ether (b.p. 60°–80°). 15 ml fractions were collected and those containing the title compound (identified using silica gel t.l.c.) were combined. Evaporation of solvent under reduced pressure from the combined fractions gave the title compound as a colourless gum (0.91 g, 2.53 mmole), [α]$_D^{20}$ = +40.1° (c 0.8 CHCl₃) ν$_{max}$ (CHCl₃); 3420, 1800, 1740, 1700(sh), 1690 cm⁻¹. δ(CDCl₃): 1.3 (m, 3H), 2.9–3.6 (m, 2H), 3.9–4.2 (m, 2H), 4.6–4.9 (m, 1H), 5.05 (d, J 1 Hz, 1H), 5.2 (s, 2H), 5.3–6 (complex, 3H), 7.32 (s, 5H), 7.9–8.2 (complex, 1H).

EXAMPLE 9

Lithium 9-O-(1-formamidoethyl)clavulanate

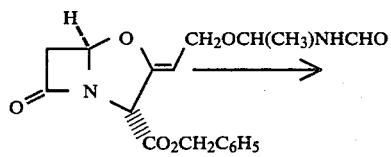

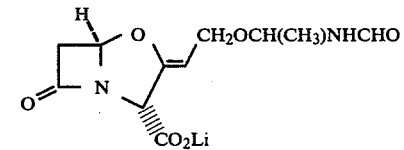

Benzyl 9-O-(1-formamidoethyl)clavulanate (900 mg, 2.5 mmole) was dissolved in tetrahydrofuran and the solution was shaken with 10% palladium-on-charcoal (300 mg) under one atmosphere of hydrogen at room temperature for 25 minutes. The catalyst was removed by filtration and was washed with tetrahydrofuran (20 ml) and water (70 ml). The pH of the filtrate was adjusted to 7.0. using 1.0 M lithium hydroxide solution (2.4 ml). The solvent was then evaporated under reduced pressure and the resulting residue was stirred with a mixture of acetone (15 ml) and ether (30 ml). The solid was collected by filtration, washed with ether, and dried in vacuo. The title compound was thus obtained as a pale yellow, amorphous powder (620 mg, 2.25 mmole), $[\alpha]_D^{20} = +35.6°$ (c 0.675, H$_2$O). $\nu_{max}$ (KBr): 1780, 1700(sh), 1690, 1620 cm$^{-1}$. $\delta$(D$_2$O): 1.25 (d, J 5.5 Hz, 3H) 3.00 (d, J 16 Hz, 1H), 3.49 (dd, J 16, 2 Hz, 1H), 4.07 (d, J 7.5 Hz, 2H), 4.6-5.1 (m, part obscured by DOH) 5.2-5.4 (m, 1H), 5.67 (m, 1H), 8.10 (m, 1H).

EXAMPLE 10

Benzyl 9-O-(2-benzyloxycarbonylaminoacetamidomethyl)-clavulanate

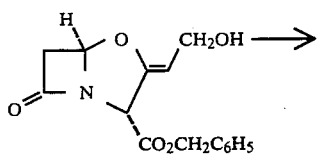

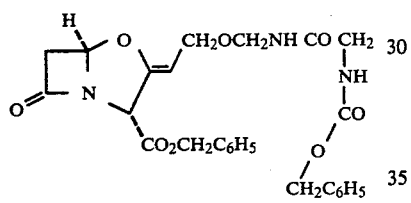

N-Acetoxymethyl-2-(benzyloxycarbonylamino)-acetamide (560 mg, 2 mmole) and benzyl clavulanate (600 mg, 2.08 mmole) were dissolved in dry benzene (30 ml). Finely powdered zinc acetate dihydrate (200 mg, 0.9 mmole) was added to the solution, and the mixture was stirred and refluxed with azeotropic removal of water for 4 hours. The mixture was cooled, diluted with ethyl acetate (100 ml) and filtered. The filtrate was washed with saturated sodium bicarbonate solution (50 ml), water (50 ml) and saturated brine (50 ml). The solution was dried (sodium sulphate) and the solvent was evaporated under reduced pressure to yield a yellow gum. The gum was chromatographed on silica gel (25 g) using 1:3→3:2 ethyl acetate/petroleum ether (b.p. 60°-80°). 15 ml fractions were collected and those containing the title compound (identified using silica gel t.l.c.) were combined. Evaporation of solvent under reduced pressure from the combined fractions gave the title compound as a colourless gum (560 mg, 1.1 mmole), $[\alpha]_D^{20} = +22.1°$ (c 0.92, CHCl$_3$). $\nu_{max}$ (CHCl$_3$):3870, 1800, 1740, 1690 cm$^{-1}$. $\delta$(CDCl$_3$): 3.03 (dd, J 16, 1 Hz, 1H), 3.40 (dd, J 16, 2 Hz, 1H), 3.80 (d, J 6 Hz, 2H), 4.06 (d, J 7 Hz 2H), 4.63 (d, J 6 Hz, 2H), 4.75 (dt, J 1,7 Hz, 1H), 5.05 (d, J 1 Hz, 1H), 5.10 (s, 2H), 5.20 (s, 2H), 5.50 (t, J 6 Hz, 1H) 5.62 (d, J 2 Hz, 1H), 6.80 (t, J 6 Hz, 1H), 7.32 (s, 10H).

EXAMPLE 11

9-O-(Glycylaminomethyl)clavulanic acid

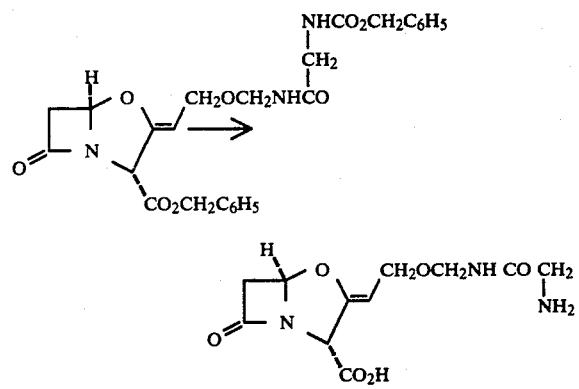

Benzyl 9-O-(2-benzyloxycarbonylaminoacetamidomethyl)clavulanate (530 mg, 1.04 mmole) was dissolved in a mixture of tetrahydrofuran (20 ml) and water (10 ml), and the solution was shaken with 10% palladium-on-charcoal (180 mg) under one atmosphere of hydrogen at room temperature for 25 minutes. The catalyst was removed by filtration and was washed well with water. The solvent was evaporated under reduced pressure from the filtrate and the resulting residue was stirred with a mixture of acetone (5 ml) and ether (10 ml). The solid was collected by filtration and was washed with ether and then dried in vacuo. The title compound was thus obtained as a very pale yellow, amorphous powder (280 mg, 0.98 mmole), $[\alpha]_D^{21} = +30.8°$ (c 0.55, H$_2$O). u$_{max}$ (KBr): 1780, 1700 (sh.), 1695, 1605, 1555 cm. $\delta$(D$_2$O): 2.90 (d, J 17 Hz, 1H), 3.35 (dd, J 17, 2 Hz, 1H), 3.65 (s, 2H), 3.97 (d, J 7 Hz, 2H), 4.3-5.0 (m, part obscured by DOH), 5.55 (d, J 2 Hz, 1H).

EXAMPLE 12

Benzyl 9-O-[(3S,4S)-2'-oxo-3'-benzyloxycarbonylaminoacetidin-4'-yl]-clavulanate and benzyl 9-O-[(3S,4R)-2'-oxo-3'-benzyloxycarbonylaminoazetidin-4'-yl]-clavulanate

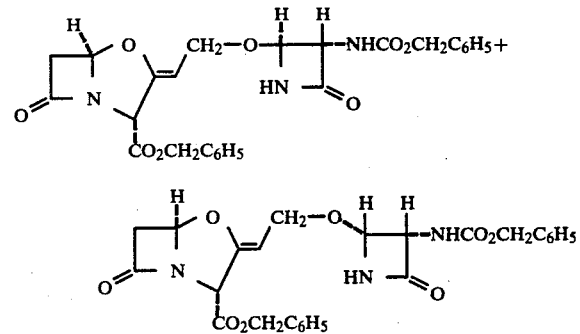

Benzyl clavulanate (600 mg, 2.07 mmole) and (3S,4S)-4-acetoxy-3-benzyloxycarbonylaminoazetidin-2-one (520 mg, 1.87 mmole) were dissolved in dry benzene (25 ml). Finely powdered zinc acetate dihydrate (200 mg) was added to the solution which was then stirred and refluxed with azeotropic removal of water for 6 hours. The mixture was cooled, diluted with ethyl acetate (100 ml) and filtered. The filtrate was washed with water (50 ml), saturated sodium bicarbonate solution (50 ml), and saturated sodium chloride solution (50 ml). The solution was dried (magnesium sulphate) and the solvent was evaporated under reduced pressure to yield a yellow gum. The gum was chromatographed on silica gel using ethyl acetate/petroleum ether (b.p. 60°-80°). Benzyl 9-O-[(3S,4S)-2-oxo-3-benzyloxycarbonylaminoazetidin-4-yl]-clavulanate was thus obtained as a colourless gum (280 mg, 29.5%), $[\alpha]_D^{21} = +12.7°$ (c 1.0, CHCl$_3$). $\nu_{max}$ (CHCl$_3$): 3420, 3310, 1790, 1505 cm$^{-1}$. δ(CDCl$_3$): 2.98 (d, J 17 Hz, 1H), 3.39 (dd, J 17 and 2 Hz, 1H), 4.15 (d, J 7 Hz, 2H), 4.37 (d, J 7.5 Hz, 1H), 4.76 (t, J 7 Hz, 1H), 4.98 (s, 1H), 5.07 (s, 3H), 5.16 (s, 2H), 5.61 (d, J 2 Hz, 1H), 5.77 (d, J 7.5 Hz, 1H), 6.98 (br.s, 1H), 7.30 and 7.32 (both s, 10H).

Benzyl 9-O-[(3S,4R)-2-oxo-3-benzyloxycarbonylaminoazetidin-4-yl]-clavulanate was also obtained as a colourless gum (290 mg, 30.5%), $[\alpha]_D^{21} = +42.0°$ (c 1.16, CHCl$_3$). $\nu_{max}$ (CHCl$_3$): 3440, 3280, 1795, 1720, 1510 cm$^{-1}$. δ(CDCl$_3$): 2.98 (d, J 16.5 Hz, 1H), 3.39 (dd, J 16.5 and 2 Hz, 1H), 4.10 (d, 7 Hz, 2H), 4.74 (t, J 7 Hz, 1H), 4.9–5.2 (m), 5.10 (s), and 5.17 (s) (total 7H), 5.5–5.7 (m, 2H), 7.05 (br.s. 1H), 7.32 (s, 10H).

EXAMPLE 13

9-O-[(3S,4S)-2'-Oxo-3'-aminoazetidin-4'-yl]clavulanic acid

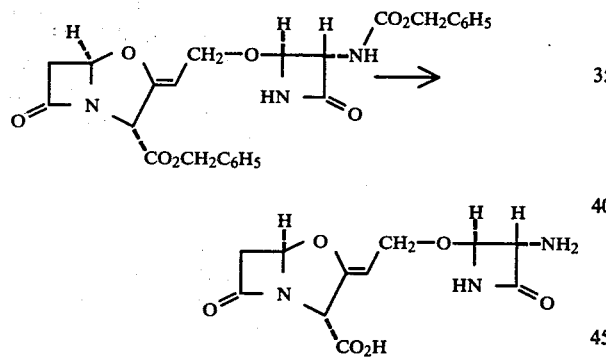

Benzyl 9-O-[(3S,4S)-2-oxo-3-benzyloxycarbonlaminoazetidin-4-yl]clavulanate (190 mg) was dissolved in a mixture of tetrahydrofuran (15 ml) and water (7 ml) and the solution was shaken with 10% palladium-on-charcoal (60 mg) under 1 atmosphere of hydrogen at room temperature for 25 minutes. The catalyst was removed by filtration and was washed with water (5×10 ml). The combined filtrate and washings were evaporated to dryness under reduced pressure. The resulting residue was stirred with acetone (5 ml) while diethyl ether (10 ml) was slowly added. The resulting precipitate was collected by filtration, was washed with ether, and dried in vacuo. The title compound was thus obtained as a pale yellow powder (100 mg), $[\alpha]_D^{22} = -19.4°$ (c 0.7, water). $\nu_{max}$ (KBr): 1775, 1690, 1600, 1385 cm$^{-1}$. δ (D$_2$O): 3.02 (d, J 17 Hz, 1H), 3.50 (dd, J 17 and 2 Hz, 1H), 4.18 (d, J 8 Hz, 2H), 5.65 (d, J 2 Hz, 1H); other signals overlapped and partially obscured by HOD absorptions.

EXAMPLE 14

9-O-[(3S,4R)-2'-Oxo-3'-aminoazetidin-4'-yl]-clavulanic acid

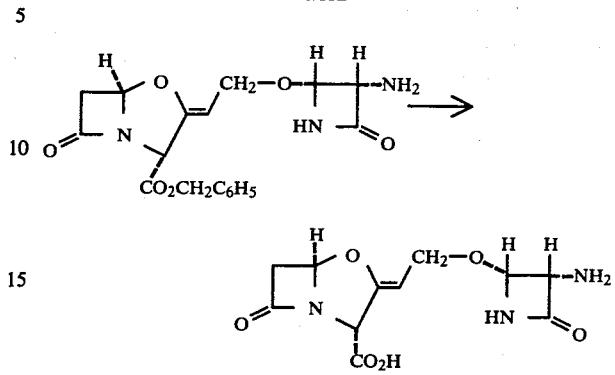

Benzyl 9-O-[(3S,4R)-2-oxo-3-benzyloxycarbonylaminoazetidin-4-yl] clavulanate (280 mg) was converted into the title compound using the process described in Example 13. The title compound was obtained as a pale yellow powder (150 mg), $[\alpha]_D^{22} = +34.7°$ (c 0.6, water) $\nu_{max}$ (KBr): 1785 (sh.), 1770, 1690, 1605, 1385 cm$^{-1}$. δ (D$_2$O): 2.95 (d, J 17 Hz, 1H), 3.45 (dd, J 17 and 2 Hz, 1H), 4.17 (d, J 7 Hz, 2H), 5.25 (d, J 4 Hz, 1H), 5.62 (d, J 2 Hz, 1H); other signals overlapped and partially obscured by HOD absorptions.

EXAMPLE 15

Benzyl 9-O-(2'-oxopyrrolidin-1'-ylmethyl)clavulanate

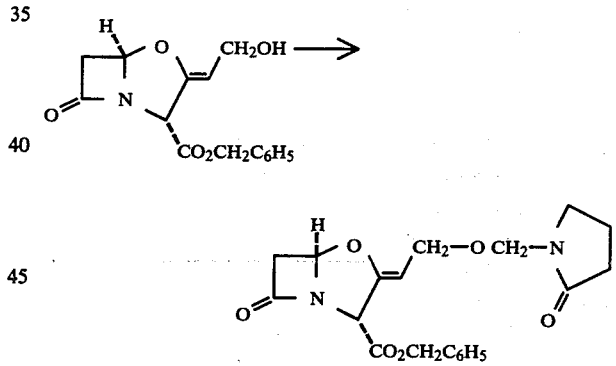

1-Hydroxymethylpyrrolidin-2-one (440 mg) and 2,6-lutidine (700 mg) were dissolved in dry tetrahydrofuran (15 ml) and the solution was stirred at −30° with exclusion of moisture while thionyl chloride (700 mg) in dry tetrahydrofuran (5 ml) was added dropwise over 5 minutes. The mixture was stirred for a further 30 minutes at −30° to −20° and was then diluted with dry benzene (50 ml) and warmed to room temperature. The mixture was filtered and the solvent was evaporated from the filtrate to yield 1-Chloromethylpyrrolidin-2-one as a yellow oil. The oil was dissolved in dry tetrahydrofuran (10 ml) and benzyl clavulanate (1.0 g) and 2,6-lutidine (420 mg) were added to the solution. The mixture was stirred at room temperature with exclusion of moisture for 1.5 hours. The mixture was diluted with ethyl acetate (100 ml) and washed with water (2×50 ml) and saturated sodium chloride solution (50 ml). The solution was dried (magnesium sulphate) and the solvent was evaporated under reduced pressure to give a pale yellow gum (1.2 g). The gum was chromatographed on silica gel using ethyl acetate/petroleum ether (b.p. 60°–80°) to give the title compound as a colourless gum (275 mg), $[\alpha]_D^{20} = +28.8°$ (c 1.0, CHCL$_3$). $\nu_{max}$ (CHCl$_3$): 1800, 1740, 1700 (sh.), 1685 cm$^{-1}$. δ (CDCl$_3$): 1.80–2.15 (m,2H), 2.30–2.50(m,2H), 3.05(d,J 16.5 Hz,1H), 3.30–3.55(m,3H), 4.03(br.d,J 7 Hz,2H), 4.66(s,2H), 4.79(dt,J 1 and 7 Hz,1H), 5.05(s, 1H) 5.18 (s, 2H), 5.65(d,J 2 Hz,1H), 7.33(s, 5H).

EXAMPLE 16

Benzyl 9-O-(2'-oxo-1'-benzyloxycarbonylmethylazetidin-4'-yl)clavulanate

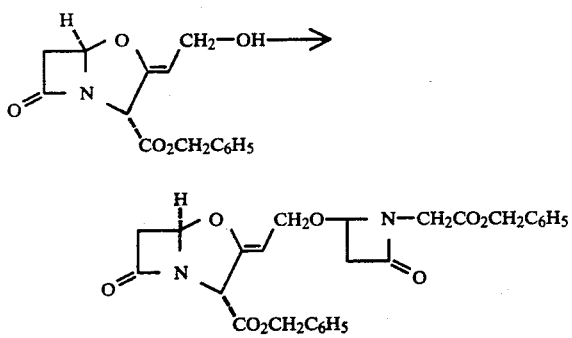

1-Benzyloxycarbonylmethyl-4-methylthioazetidin-2-one (2.65 g) was dissolved in methylene dichloride (50 ml) and the solution was stirred and ice cooled while a solution of chlorine (0.71 g) in carbon tetrachloride (7 ml) was added in one portion. The mixture was stirred for 3 minutes and then the solvent was evaporated under reduced pressure to yield 1-benzyloxycarbonylmethyl-4-chloroazetidin-2-one as a pale yellow oil (2.65 g).

The above chloride was dissolved in dry methylene dichloride (25 ml) and to the solution was added benzyl clavulanate (2.89 g), 2,6-lutidine (30 mg), dry silver oxide (2.5 g), and 4A molecular sieve powder (2.5 g). The mixture was stirred at room temperature with exclusion of moisture for 40 hours. The mixture was filtered and the solvent was evaporated from the filtrate. The resulting gum was dissolved in ethyl acetate (100 ml) and the solution was washed with dilute citric acid solution (50 ml) and water (50 ml). The solution was dried (magnesium sulphate) and the solvent was evaporated under reduced pressure to yield a dark coloured gum. The gum was chromatographed on silica gel (25 g) using ethyl acetate/petroleum ether (b.p. 60°–80°) to yield the title compound as a pale yellow gum (3.05 g), $[\alpha]_D^{20} = +24.6°$ (c 1.1, CHCl$_3$). $\nu_{max}$ (CHCl$_3$): 1800, 1760 (sh.), 1740, 1700 (sh.) cm$^{-1}$. δ (CDCl$_3$): 2.7–3.2 (complex, 3H), 3.44 (dd, J 16 and 2 Hz, 1H), 3.70 (d, J 19 Hz, 1H), 4.12 (d, J 7 Hz, 2H), 4.25 (d, J 19 Hz, 1H), 4.75 (t, J 7 Hz, 1H), 5.05 (s, 1H), 5.14 (s, 2H), 5.17 (s, overlapped by m, 3H), 5.63 (d, J 2 Hz, 1H), 7.33 (s, 10H).

EXAMPLE 17

Dilithium 9-O-(2'-oxo-1'-carboxymethylazetidin-4'-yl)clavulanate

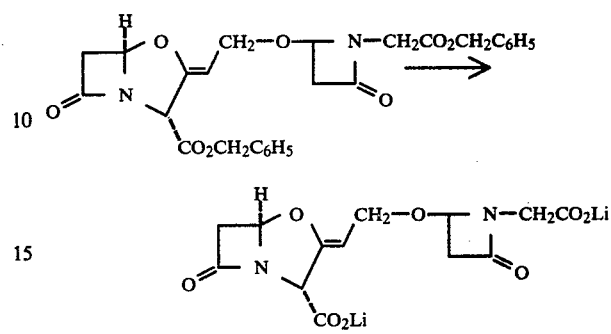

Benzyl 9-O-(2'-oxo-1'-benzyloxycarbonylmethylazetidin-4'-yl)clavulanate (1.0 g) was dissolved in tetrahydrofuran (40 ml) and the solution was shaken with 10% palladium-on-charcoal (350 mg) under 1 atmosphere of hydrogen at room temperature for 25 minutes. The catalyst was removed by filtration and was washed with tetrahydrofuran (35 ml) and water (75 ml). The pH of the filtrate was adjusted to 7.0 by dropwise addition of 1.0M lithium hydroxide solution. The solvent was evaporated under reduced pressure and the resulting residue was dissolved in methanol (5 ml). Slow addition of acetone (15 ml) and then ether (40 ml) to this solution gave a precipitate which was collected by filtration, washed with ether and dried in vacuo. The title compound was thus obtained as a colourless powder (550 mg), $[\alpha]_D^{21} = +27.8°$ (c 0.6, water). $\nu_{max}$ (KBr): 1780, 1745, 1690, 1605, 1400, 1310 cm$^{-1}$. δ (D$_2$O): 2.83 (br.d., J 16 Hz, 1H), 3.10 (br.d, J 17 Hz, 1H), 3.22 (dd, J 16 and 4 Hz, 1H), 3.57 (dd, J 17 and 2 Hz, 1H), 3.65 (d, J 18 Hz, 1H), 3.98 (d, J 18 Hz, 1H), 4.25 (d, J 7.5 Hz, 2H), 4.90 (t, J 7.5 Hz, 1H), 4.95 (s, 1H), 5.26 (dd, J 4 and 2 Hz, 1H), 5.70 (d, J 2 Hz, 1H).

EXAMPLE 18

Benzyl 9-O-(N-formyl-N-methylaminomethyl)clavulanate

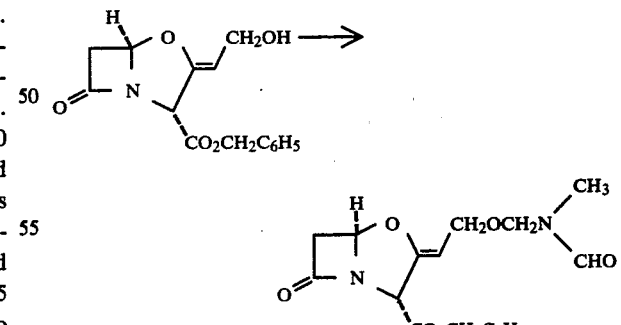

Benzyl clavulanate (2.89 g) and lithium tetrafluoroborate (150 mg) were dissolved in dry N,N-dimethylformamide and the resulting solution was ice-cooled while being electrolysed (2×1.5 sq. cm. platinum foil electrodes placed 1 mm apart) using a current of 300 mA for 2.25 hours. The solution was diluted with ethyl acetate (150 ml) and was washed with water (4×50 ml) and saturated sodium chloride solution (50 ml). The solution was dried (magnesium sulphate) and the solvent was evaporated under reduced pressure to give a yellow gum (2.15 g). The gum was chromatographed on silica gel using ethyl acetate/petroleum ether (b.p. 60°–80°) to give the title compound as a pale yellow gum (740 mg), $[\alpha]_D^{20} = +38.3°$ (c 1.05, CHCl$_3$). $\nu_{max}$ (CHCl$_3$): 1800, 1740, 1690 (sh), 1680 cm$^{-1}$. δ (CDCl$_3$): 2.85 (s, 3H), 3.05 (dd, J 16 and 1 Hz, 1H), 3.05 (dd, J 16 and 2 Hz, 1H), 3.95 (d, J 7 Hz, 2H), 4.50 (s, 2H), 4.70 (dt, J 1 and 7 Hz, 1H), 5.05 (d, J 1 Hz, 1H), 5.13 (s, 2H), 5.65 (dd, J 2 and 1 Hz, 1H), 7.30 (s, 5H), 8.00 (s, 1H).

EXAMPLE 19

Lithium 9-O-(N-formyl-N-methylaminomethyl)clavulanate

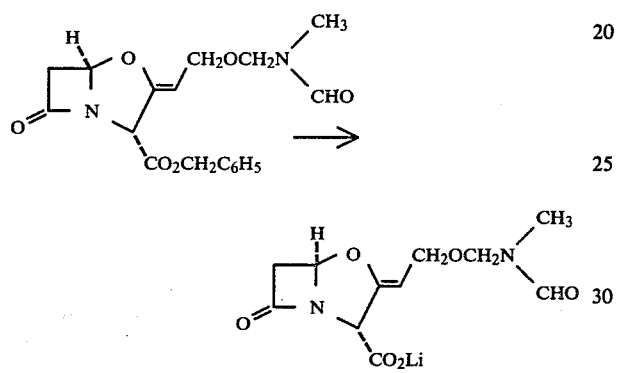

Benzyl 9-O-(N-formyl-N-methylaminomethyl)clavulanate (510 mg) was dissolved in tetrahydrofuran (40 ml) and the solution was shaken with 10% palladium-on-charcoal (150 mg) under 1 atmosphere of hydrogen at room temperature for 25 minutes. The catalyst was removed by filtration and was washed with tetrahydrofuran (50 ml) and water (100 ml). The pH of the filtrate was adjusted to 7.0 by dropwise addition of 1.0M lithium hydroxide solution. The solvent was evaporated under reduced pressure and the resulting residue was stirred with acetone (10 ml) while ether (20 ml) was slowly added. The precipitate was collected by filtration, washed with ether and dried in vacuo to give the title compound as a pale yellow powder (275 mg), $[\alpha]_D^{21} = +47.6°$ (c 0.5, water). $\nu_{max}$ (KBr): 1780, 1690, 1660, 1610 cm$^{-1}$. δ (D$_2$O): 2.90 (s, 3H), 3.15 (d, J 16 Hz, 1H), 3.65 (dd, J 16 and 2 Hz, 1H), 4.15 (d, J 7 Hz, 2H), 4.85 (s, 2H), 4.6–5.0 (m, part obscured by HOD absorption), 5.75 (d, J 2 Hz, 1H), 8.15 (s, 1H).

EXAMPLE 20

Benzyl 9-O-(N-acetyl-N-methylaminomethyl)clavulanate

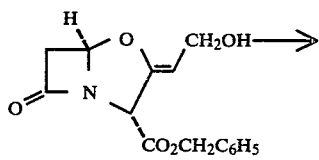

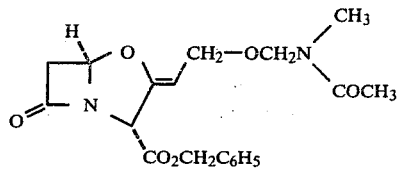

A solution of benzyl clavulanate (2.0 g) and lithium tetrafluoroborate (0.2 g) in N,N-dimethylacetamide (15 ml) was converted into the title compound using the process described in Example 18. The title compound was obtained as a pale yellow gum (300 mg), $[\alpha]_D^{20} = +40.5°$ (c 1.0, CHCl$_3$). $\nu_{max}$ (CHCl$_3$): 1800, 1740, 1695, 1650 cm$^{-1}$.

EXAMPLE 21

Lithium 9-O-(2'-oxopyrrolidin-1'-ylmethyl)clavulanate

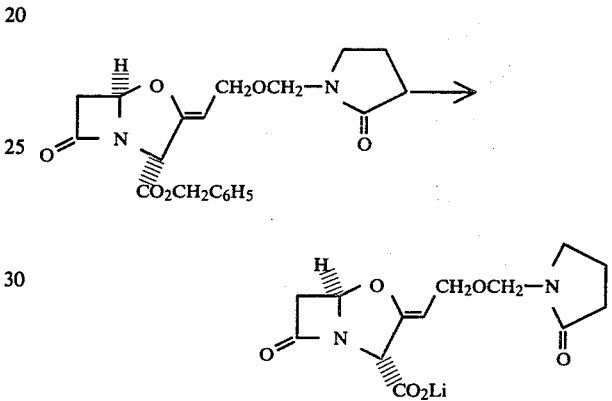

Benzyl 9-O-(2-oxopyrrolidin-1-ylmethyl)clavulanate (270 mg) was dissolved in tetrahydrofuran (20 ml) and the solution was shaken with 10% palladium-on-charcoal (100 mg) under one atmosphere of hydrogen at room temperature for 35 minutes. The catalyst was removed by filtration and was washed with tetrahydrofuran (30 ml) and water (50 ml). The filtrate was brought to pH 7.0 by dropwise addition of 1.0M lithium hydroxide solution and then the solvent was evaporated under reduced pressure. The resulting residue was dissolved in methanol (2 ml), and acetone (5 ml) followed by ether (15 ml) was slowly added. The resulting precipitate was collected by filtration, washed with ether, and dried in vacuo. The title compound was thus obtained as a pale yellow powder (195 mg), $[\alpha]_D^{20} = +30.6°$ (c 0.55, water). $\nu_{max}$ (KBr): 1780, 1705, 1675, 1610 cm$^{-1}$. δ (D$_2$O): 1.9–2.2 (2H, m), 2.35–2.55 (2H, m), 3.07 (1H, d, J 17.5 Hz), 3.4–3.7 (3H, m), 4.12 (2H, d, J 7.5 Hz), 4.70 (2H, s), 4.87 (1H, t, J 7.5 Hz), 4.95 (1H, s), 5.69 (1H, d, J 2 Hz).

EXAMPLE 22

Lithium 9-O-(N-acetyl-N-methylaminomethyl)clavulanate

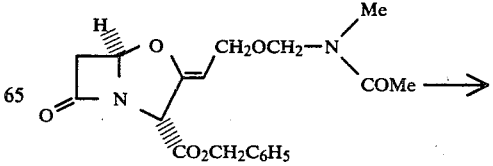

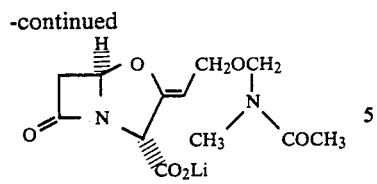

Benzyl 9-O-(N-acetyl-N-methylaminomethyl)-clavulanate (290 mg) in tetrahydrofuran (20 ml) was shaken with 10% palladium-on-charcoal (100 mg) under one atmosphere of hydrogen at room temperature for 30 minutes. The catalyst was removed by filtration and was washed with tetrahydrofuran (30 ml) and water (50 ml). The filtrate was brought to pH 7.0 by dropwise addition of 1.0M lithium hydroxide solution and then the solvent was evaporated under reduced pressure. The resulting yellow gum was dissolved in methanol (2 ml) and to the solution acetone (5 ml) and then ether (15 ml) were slowly added. The precipitate was collected by filtration, washed with ether, and dried in vacuo to give the title compound as a pale yellow powder (200 mg), $[\alpha]_D^{20} = +30.8°$ (c 0.525, water). $\nu_{max}$ (KBr): 1780, 1690, 1670, 1615 cm$^{-1}$. δ (D$_2$O): 2.06 and 2.08 (3H, both s), 2.86 and 2.98 (3H, both s), 3.00 (1H, d, J 17.5 Hz), 3.52 (1H, dd, J 17.5 and 2 Hz), 4.05 and 4.10 (2H, both d, J 7.5 Hz), 4.73 and 4.75 (2H both s), ca 4.90 (2H complex), 5.65 (1H, d, J 2 Hz).

EXAMPLE 23

Sodium 9-O-[(3S,4R)-3'-phenoxyacetamido-2'-oxoazetidin-4'-yl]-clavulanate

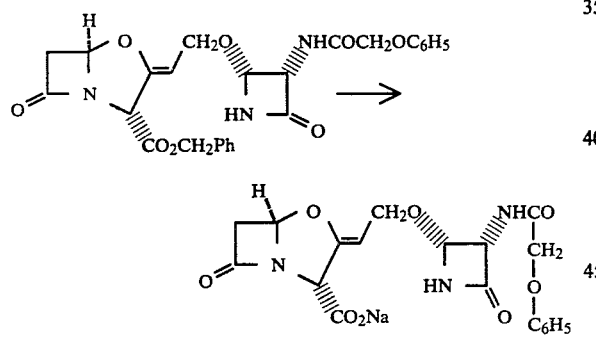

Benzyl 9-O-[(3S, 4R)-3'-phenoxyacetamido-2'-oxoazetidin-4'-yl]-clavulanate (237 mg) was converted into the title compound using the process described in Example 25. The title compound was obtained as a pale yellow powder (172 mg). $\nu_{max}$ (KBr): 1770, 1670 and 1610 cm$^{-1}$. δ (D$_2$O): 2.94 (1H, d, J 17 Hz), 3.44 (1H, dd, J 3 & 17 Hz), 4.07 (2H, d, J 7 Hz), 4.79 (1H, t, J 7 Hz), 4.89 (1H, s), 5.13 (1H, d, J 4 Hz), 5.23 (1H, d, J 4 Hz), 5.62 (1H, d, J 3 Hz), 6.8–7.5 (5H, m).

EXAMPLE 24

Benzyl 9-O-[acetamidomethyl]-clavulanate

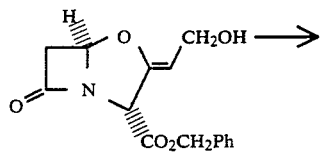

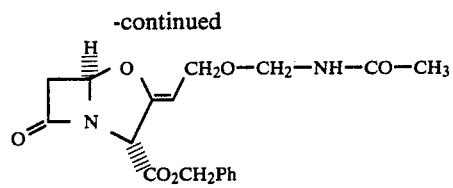

A solution of benzyl clavulanate (1.445 g) and acetamidomethyl acetate (980 mg) in benzene (15 ml) was refluxed using a Dean and Stark water separator for 15 mins. Zinc acetate dihydrate (110 mgs) was then added and the mixture refluxed for a further 2 hours. The solution was then cooled and filtered, and the solvent was evaporated under reduced pressure. The product was isolated from the residue by column chromatography using gradient elution (Kieselgel; 1:1 ethyl acetate:cyclohexane going to neat ethyl acetate). The title compound was thus obtained as a yellow gum (1.017 g). $\nu_{max}$ (film): 3320, 1805, 1750 and 1690 cm$^{-1}$. δ (CDCl$_3$): 2.01 (3H, s), 3.07 (1H, d, J 17 Hz), 3.53 (1H, dd, J 3 and 17 Hz), 4.15 (2H, d, J 7 Hz), 4.69 (2H, d, J 7 Hz), 4.76 (1H, t, J 7 Hz), 5.14 (1H, broad s), 5.25 (2H, s), 5.74 (1H, d, J 3 Hz), 6.48 (1H, broad), 7.43 (5H, s).

EXAMPLE 25

Sodium 9-O-[(3S, 4S)-3'-phenoxyacetamido-2'-oxoazetidin-4'-yl]-clavulanate

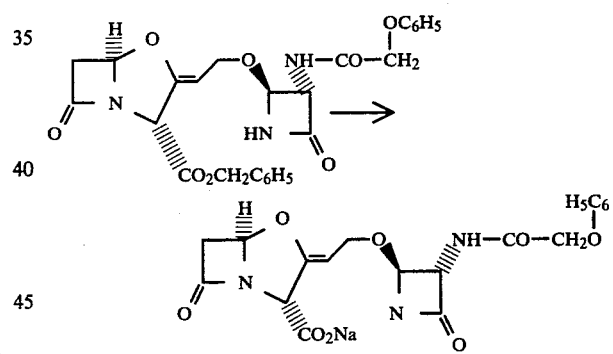

A solution of benzyl 9-O-[(3S, 4S)-3'-phenoxyacetamido-2'-oxoazetidin-4'-yl]-clavulanate (384 mgs) in tetrahydrofuran (20 ml) was shaken with 10% palladium-on-charcoal (80 mg) under 1 atmosphere of hydrogen at room temperature for 1 hour. The solution was filtered through celite and the filter cake was washed with tetrahydrofuran. The combined filtrates were treated with a solution of sodium bicarbonate (63 mgs) in water. Most of the tetrahydrofuran was removed on a rotary evaporator, and the remaining aqueous solution was washed three times with ethyl acetate, filtered through celite and evaporated. The residue was dried over phosphorus pentoxide to give the title compound as a pale yellow amorphous powder (270 mg). $\nu_{max}$ (KBr): 1765, 1665 and 1610 cm$^{-1}$. δ(D$_2$O): 2.98 (1H, d, J 17 Hz), 3.45 (1H, dd, J 3 & 17 Hz), 4.18 (2H, d, J 8 Hz), 4.52 (2H, s), 4.65–5.05 (2H, m), 4.90 (1H, s), 5.15 (1H, s), 5.67 (1H, d, J 3 Hz), 6.8–7.5 (5H, m).

EXAMPLE 26

Sodium 9-O-(acetamidomethyl)-clavulanate

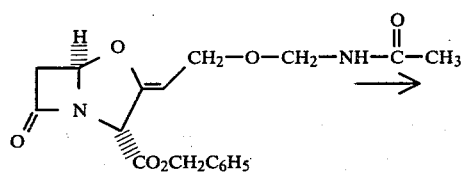

A solution of benzyl 9-O-(acetamidomethyl)clavulanate (1.017 gm) in tetrahydrofuran (30 mls) was shaken with 10% palladium-charcoal (300 mgs) under 1 atmosphere of hydrogen at room temperature for 15 mins. The solution was filtered through celite and the filter cake washed with tetrahydrofuran. A solution of sodium bicarbonate (237 mgs) in water was then added and most of the tetrahydrofuran was removed under reduced pressure. The remaining aqueous solution was extracted three times with ethyl acetate, filtered through celite, and the water was evaporated under reduced pressure. The residue was dried over phosphorus pentoxide to yield the title compound as an off-white amorphous powder (652 mg). $\nu_{max}$ (KBr): 1783, 1665 and 1620 cm$^{-1}$. $\delta$(D$_2$O): 2.05 (3H, s), 3.13 (1H, d, J 17 Hz), 3.61 (1H, dd, J 3 & 17 Hz), 4.17 (2H, d, J 7 Hz), 4.93 (1H, broad t, J 7 Hz), 5.00 (1H, s), 5.77 (1H, d, J 3 Hz).

EXAMPLE 27

Lithium 9-O-(2'-oxoazetidin-4'-yl)-clavulanate

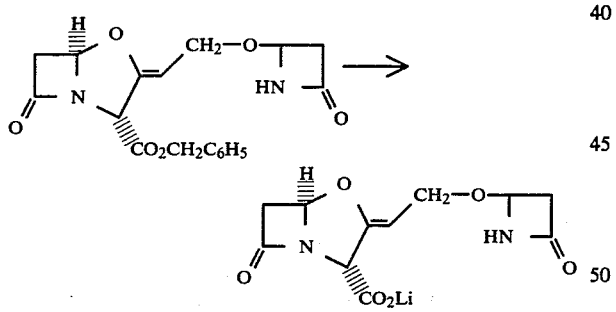

Benzyl 9-O-(2'-oxoazetidin-4'-yl)-clavulanate (17.2 g., 48 mmole) was divided into four approximately equal batches. Each batch (3.8–4.7 g) was dissolved in tetrahydrofuran (100–120 ml) and was shaken with 10% palladium-on-charcoal (1.3–1.5 g) at room temperature under 1 atmosphere of hydrogen. In all cases the theoretical amount of hydrogen was taken up at a steady rate over 20–25 minutes and then hydrogen uptake ceased. The catalyst was removed by filtration and was washed with tetrahydrofuran (50 ml) and water (150 ml). The combined filtrates were brought to pH 7.0 by dropwise addition of 1.0 M lithium hydroxide (45 ml). From the resulting solution the solvent was evaporated under reduced pressure (rotary evaporator at <30° C.). To the resulting pale yellow syrup, acetone (200 ml) was added slowly with stirring and then ethyl acetate (300 ml) was slowly added. The resulting precipitate was collected by filtration, was washed with ether (3×30 ml), and was dried over phosphorus pentoxide in vacuo for 17 hours. The title compound was thus obtained as a very pale yellow amorphous powder (11.75 g, 43 mmole), $[\alpha]_D^{20} = +25.6°$ (c 1.0, water). $\nu_{max}$ (KBr): 1775, 1750 (sh.), 1700, 1620 cm$^{-1}$.

EXAMPLE 28

9-O-(2'-Oxoazetidin-4'-yl)-clavulanic acid

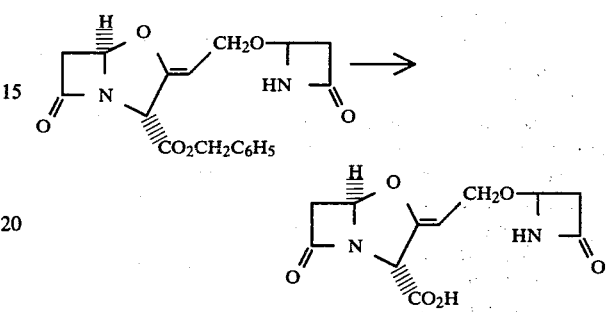

Benzyl 9-O-(2'-oxoazetidin-4'-yl)-clavulanate (2.0 g) was dissolved in tetrahydrofuran (40 ml) and the solution was shaken with 10% palladium-on-charcoal (0.5 g) under one atmosphere of hydrogen at room temperature for 20 minutes. The catalyst was removed by filtration and was washed with tetrahydrofuran (3×20 ml). From the filtrate the solvent was evaporated under reduced pressure to yield the title compound as a colourless gum (1.57 g; at least 90% pure as judged by n.m.r. and t.l.c.), $[\alpha]_D^{20} = +27.1°$ (c 1.0, ethyl acetate). On thin layer chromatography (silica gel; 50:50:7 chloroform:acetone:acetic acid) the produce produced a single zone (Rf=0.12) when the plate was sprayed with a 0.4% solution of p-dimethylaminobenzaldehyde in ethanol containing 1% HCl and warmed. $\nu_{max}$(CHCl$_3$): 3400–2400, 1800, 1760 (sh.), 1740, 1700 (sh.)cm$^1$. $\delta$(CD$_3$SOCD$_3$): 2.60 (1H, d, J 15 Hz), 2.98 (1H, dd, J 15 and 3 Hz), 3.09 (1H, d, J 17 Hz), 3.67 (1H, dd, J 17 and 2 Hz), 4.06 (2H, d, J 7 Hz), 4.80 (1H, t, J 7 Hz), 5.00 (1H, d, J 3 Hz), 5.12 (1H, s), 5.75 (1H, d, J 2 Hz), 7.2–8.2 (br., exchanges with D$_2$O), 8.60 (1H, br.s, exchanges with D$_2$O).

EXAMPLE 29

Potassium 9-O-(2'-oxoazetidin-4'-yl)-clavulanate

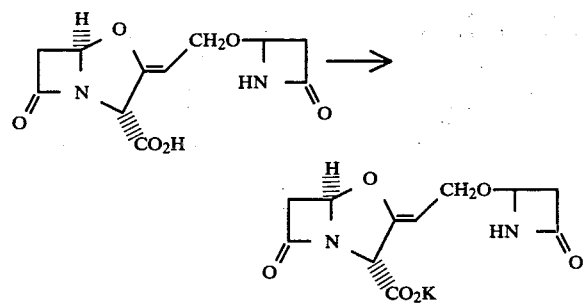

9-O-(2'-Oxoazetidin-4'-yl)-clavulanic acid (0.79 g) was dissolved in a mixture of tetrahydrofuran (30 ml) and water (30 ml). The solution was stirred while 1.0 M potassium hydroxide solution was added dropwise until the solution was at pH 7.2. The solvent was then evaporated under reduced pressure and the resulting yellow gum was dissolved in methanol (5 ml). To this solution, acetone (15 ml) and then ether (20 ml) were slowly added. The resulting precipitate was collected by filtration, was washed with ether, and dried over phosphorus pentoxide in vacuo. The title compound was thus obtained as a pale yellow powder (0.80 g), $[\alpha]_D^{20} = +20.0°$ (c 0.85, water). $\nu_{max}$ (KBr): 1780–1750 (br.), 1690 (sh.), 1655 (sh.), 1615 cm$^{-1}$.

EXAMPLE 30 t-Butylammonium 9-O-(2'-oxoazetidin-4'-yl)-clavulanate

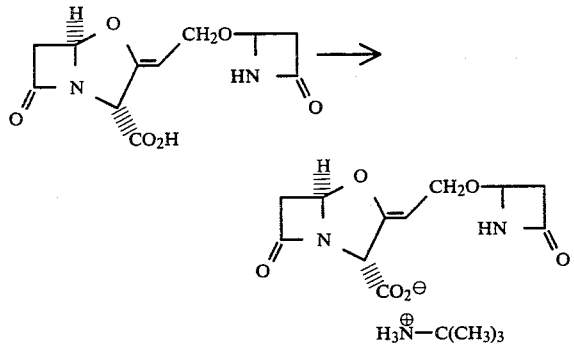

9-O-(2'-Oxoazetidin-4'-yl)-clavulanic acid (0.70 g) was dissolved in dry tetrahydrofuran (30 ml) and the solution was stirred while t-butylamine (0.18 g) was added dropwise. The resulting clear colourless solution was concentrated to ca 10 ml by evaporation of solvent under reduced pressure. Petroleum ether (b.p. 60°–80°) was then added slowly until the solution just remained cloudy. The mixture was cooled to 4° and kept at that temperature for 1.5 hours. The resulting crystals were collected by filtration, washed with 1:1 tetrahydrofuran/petroleum ether, and dried in vacuo. The title salt was thus obtained as very small colourless prisms (0.71 g), m.p. 124°–126°, $[\alpha]_D^{20} = +24.4°$ (c 0.9, ethanol). $\nu_{max}$ (KBr): 1790, 1760, 1690, 1625, 1585, 1390, 1300, 1195 cm$^{-1}$.

A sample (100 mg) of the above salt was dissolved in dry ethanol (1 ml) and 4:1 ether/pentane (5 ml) was added slowly. The mixture was cooled to 4° for 1 hour and then the crystals were collected by filtration, washed with 4:1 ether/pentane, and dried over phosphorus pentoxide in vacuo for 17 hours. The salt was thus obtained as colourless prisms (85 mg), m.p. 127°–129°, $[\alpha]_D^{20} = +25.8°$ (c 0.875, ethanol).

EXAMPLE 31

N,N-Dicyclohexylammonium 9-O-(2'-oxoazetidin-4'-yl)clavulanate

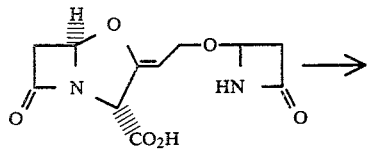

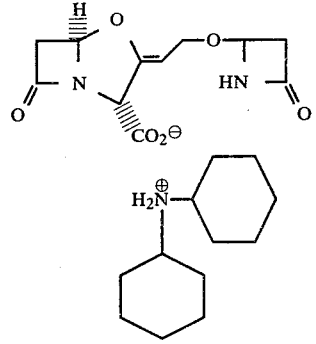

9-O-(2'-Oxoazetidin-4'-yl)-clavulanic acid (from 0.6 g benzyl ester) in tetrahydrofuran (30 ml) was treated with N,N-dicyclohexylamine (0.3 g) at room temperature. The solution was concentrated to 10 ml by evaporation of solvent under reduced pressure. Ether (10 ml) and then n-pentane (20 ml) were slowly added to the solution. The precipitate was collected by filtration, washed with ether (2×5 ml), and dried in vacuo to give the title compound as a colourless powder (0.53 g), $[\alpha]_D^{21} = +16.0°$ (c 1.1, EtOH). $\nu_{max}$ (KBr): 1775, 1750, 1690, 1615 cm$^{-1}$.

EXAMPLE 32

Magnesium di[9-O-(2'-oxoazetidin-4'-yl)clavulanate]

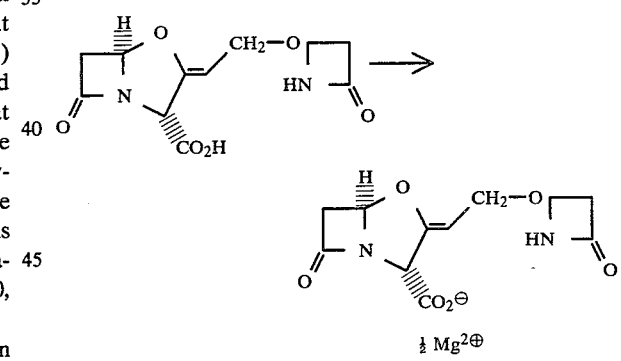

9-O-(2'-Oxoazetidin-4'-yl)clavulanic acid (from 0.6 g benzyl ether) in tetrahydrofuran (30 ml) and water (30 ml) was treated with magnesium oxide (35 mg) and the mixture was stirred for 0.5 hour at room temperature. During this time the pH of the solution went from 3.0 to 7.3 The mixture was filtered and the solvent was evaporated from the filtrate under reduced pressure to give a yellow gum. The gum was dissolved in cold methanol (1 ml) and acetone (5 ml) and then ether (10 ml) were slowly added to the solution. The precipitate was collected by filtration, washed with acetone, and dried in vacuo over phosphorus pentoxide for 16 hours. The title compound was thus obtained as a very pale yellow powder (435 mg), $[\alpha]_D^{21} = +22.4°$ (c 1.0, water). $\nu_{max}$ (KBr): 1780, 1750, 1690, 1605 cm$^{-1}$.

EXAMPLE 33

Pivaloyloxymethyl 9-O-(2'-oxoazetidin-4'-yl)-clavulanate

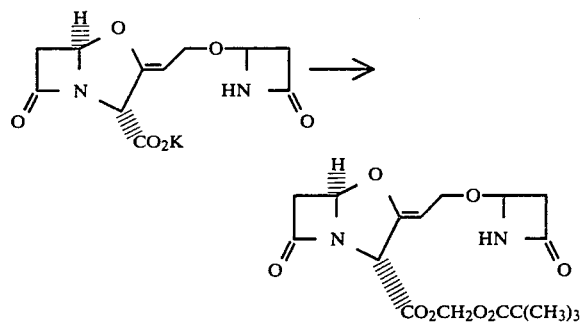

Potassium 9-O-(2'-oxoazetidin-4'-yl)-clavulanate (400 mg) was dissolved in dry N,N-dimethylformamide (4 ml) and pivaloyloxymethyl bromide (330 mg) was added to the solution. The mixture was stirred at room temperature with exclusion of moisture for 17 hours. The mixture was diluted with ethyl acetate (50 ml) and was washed with water (3×20 ml) and saturated brine (20 ml). The solution was dried (sodium sulphate) and the solvent was evaporated under reduced pressure to yield a yellow gum (350 mg). The gum was chromatographed on silica gel (20 g) using gradient elution from 1:2 to 3:2 ethyl acetate/petroleum ether (b.p. 60°-80°). The title compound was thus obtained as a colourless gum (50 mg), $[\alpha]_D^{20} = +21.9°$ (c 1.0, CHCl$_3$). $\nu_{max}$ (CHCl$_3$); 3420, 3200, 1800, 1765, 1700 cm$^{-1}$. $\delta$(CDCl$_3$): 1.21 (9H, s), 2.82 (1H, d, J 15 Hz), 2.95-3.25 (2H, complex), 3.52 (1H, dd, J 17 and 2.5 Hz). 4.14 (2H, d, J 7 Hz), 4.81 (1H, t, J 7 Hz), 5.00-5.15 (2H, complex), 5.65-5.90 (3H, complex), 6.90 (1H, br.s).

EXAMPLE 34

Benzyl 9-O-(2'-oxo-1'-methylazetidin-4'-yl)-clavulanate

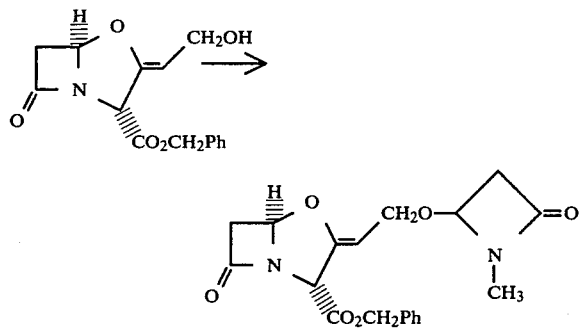

1-Methyl-4-methylthioazetidin-2-one (0.8 g) was dissolved in dry methylene dichloride (25 ml) and the solution was stirred and ice-cooled while a solution of chlorine (0.45 g) in carbon tetrachloride (3.5 ml) was added in one portion. The mixture was stirred for 3 minutes and then the solvent was evaporated under reduced pressure to yield 4-chloro-1-methylazetidin-2-one as a colourless oil.

The chloride was added to a solution of benzyl clavulanate (1.8 g) and 2,6-lutidine (0.65 g) in dry tetrahydrofuran and the mixture was stirred at room temperature with exclusion of moisture for 24 hours. The mixture was filtered and the solid was washed with ethyl acetate. The solvent was evaporated from the filtrate under reduced pressure and the resulting residue was dissolved in ethyl acetate (100 ml). The solution was washed with dilute citric acid solution, dilute sodium bicarbonate solution, water, and saturated brine. The solution was dried (magnesium sulphate) and the solvent was evaporated under reduced pressure to yield a yellow gum (2.0 g). The gum was chromatographed on silica gel (25 g) using gradient elution from 1:3 to 2:3 ethyl acetate/petroleum ether (b.p. 60°-80°). The title compound was thus obtained as a colourless gum (0.4 g). (Found: M+, 372.1321; C$_{19}$H$_{20}$N$_2$O$_6$ requires 372.1319) $[\alpha]_D^{21} = +36.0°$ (c 1.0, CHCl$_3$). $\nu_{max}$ (CHCl$_3$): 1803, 1750 1698 cm$^{-1}$. $\delta$(CDCl$_3$): 2.77 (3H, s) overlapping 2.65-2.95 (2H, m), 3.03 (1H, d, J 17 Hz), 3.48 (1H, dd, J 17 and 2 Hz), 4.14 (2H, d, J 7 Hz), 4.70-4.90 (2H, complex), 5.08 (1H, s), 5.18 (2H, s), 5.68 (1H, d, J 2 Hz), 7.32 (5H, s). m/e: 372 (M+, 2%), 272 (70), 230 (15), 91 (100).

EXAMPLE 35

Lithium 9-O-(2'-oxo-1'-methylazetidin-4'-yl)-clavulanate

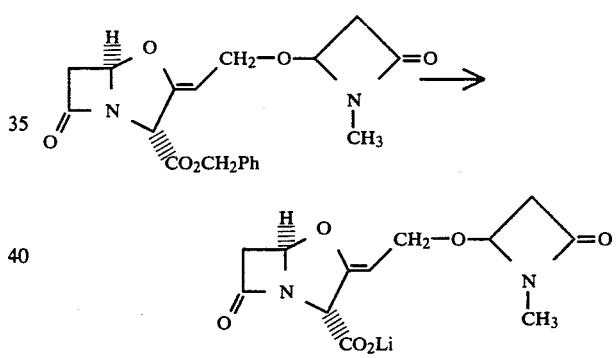

Benzyl 9-O-(2'-oxo-1'-methylazetidin-4'-yl)clavulanate (0.4 g) was dissolved in tetrahydrofuran (30 ml) and the solution was shaken with 10% palladium-on-charcoal (0.13 g) under one atmosphere of hydrogen at room temperature for 25 minutes. The catalyst was removed by filtration and was washed with 1:1 tetrahydrofuran/water (3×10 ml). The filtrate was brought to pH 7.1 by dropwise addition of 0.2 M lithium hydroxide. The solvent was removed from the filtrate under reduced pressure and the resulting residue was dissolved in methanol (2 ml), and acetone (5 ml) and ether (15 ml) were slowly added. The precipitate was collected by filtration, washed with ether, and dried in vacuo. The title salt was thus obtained as a colourless powder (0.28 g), $[\alpha]_D^{20} = +26.4°$ (c 0.55, water). $\nu_{max}$ (KBr): 1775, 1750, 1690, 1615 cm$^{-1}$. $\delta$(D$_2$O): 2.75 (3H, s) overlapping 2.65-3.05 (2H, m), 3.06 (1H, d, J 17 Hz), 3.53 (1H, dd, J 17 and 2 Hz), 4.23 (2H, d, J 7 Hz), 4.80-5.00 (2H, complex), 5.07 (1H, d, J 3.5 Hz), 5.68 (1H, d, J 2 Hz).

EXAMPLE 36

Methyl 9-O-(2'-oxoazetidin-4'-yl)clavulanate

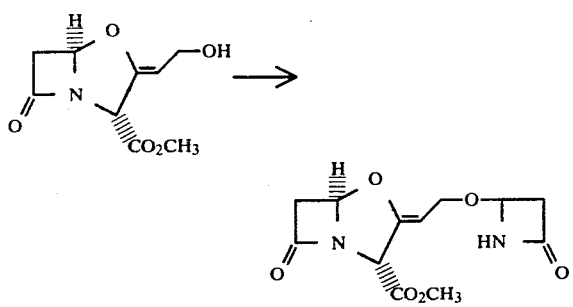

Finely powdered zinc acetate dihydrate (0.55 g) was suspended in dry benzene (25 ml) and the mixture was stirred and refluxed with azeotopic removal of water for 30 mins. A solution of methyl clavulanate (1.06 g) and 4-acetoxyazetidin-2-one (0.65 g) in dry benzene (5 ml) was then added and stirring and refluxing were continued for a further 5 hours. The mixture was cooled and filtered, the solid being washed well with more benzene. The filtrate and washings were washed with sodium bicarbonate solution and saturated brine. The solution was dried (sodium sulphate) and the solvent was evaporated under reduced pressure to yield a yellow gum. The gum was chromatographed on silica gel using gradient elution from 1:3 to 4:1 ethyl acetate/cyclohexane. The title compound was thus obtained as a colourless gum (0.71 g). δ(CDCl$_3$): 2.70–3.25 (3H, complex), 3.49 (1H, dd, J 17 and 3 Hz), 3.78 (3H, s), 4.15 (2H, d, J 7 Hz), 4.82 (1H, br. t, J 7 Hz), 5.00–5.15 (2H, complex), 5.68 (1H, d, J 3 Hz), 6.80 (1H, br.s).

EXAMPLE 37

Lithium 9-O-(2'-oxoazetidin-4'-yl)clavulanate

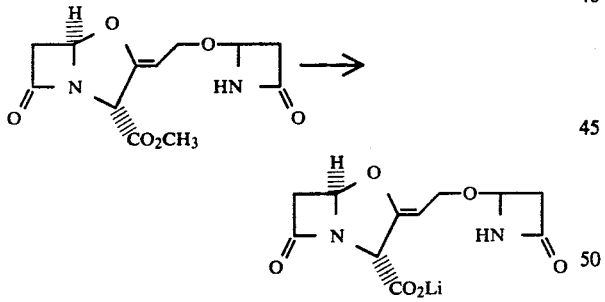

Methyl 9-0-(2'-oxoazetidin-4'-yl)clavulanate (0.2 g) was dissolved in tetrahydrofuran (10 ml) and water (25 ml) was added to the solution. The mixture was stirred at room temperature and the pH was brought to 8.5 by addition of 0.25 M lithium hydroxide. The pH of the mixture was maintained at 8.5 for 1 hour and was then raised to 9.5 and maintained there for a further 0.5 hour, by addition of 0.25 M lithium hydroxide (total=2.3 ml) The solvent was removed by evaporation under reduced pressure and the resulting residue was chromatographed on cellulose powder (Whatman CC31) using an eluent the top phase of 5:1:5 n-butanol/ethanol/water. 10 ml fractions were collected and those containing the title compound were recognised using t.l.c. These were combined and evaporated to dryness under reduced pressure. The title salt was thus obtained as a colourless powder (55 mg). ν$_{max}$ (KBr): 1770, 1745, 1690, 1620 cm$^{-1}$.

EXAMPLE 38

Compositions (a) Sterile sodium 9-O-(azetidin-2'-yl)clavulanate (100 mg) may be dissolved in sterile water for injection BP (1 ml) to form a solution for injection. The 9-0-(azetidin-2'-on-4'-yl)clavulanate may have been sealed in a vial in conventional manner.

(b) Sterile sodium 9-O-(azetidin-2'-on-4'-yl)clavulanate (80 mg) and sterile sodium amoxycillin (equivalent to 250 mg) may be dissolved in sterile water for injection BP (1 ml) to form a solution for injection. The two compounds may have been sealed into a vial together in conventional manner.

(c) Soduim 9-O-(azetidin-2'-on-4'-yl)clavulanate (125 mg) may be mixed with lactose (20 mg) and magnesium stearate and the mixture filled into a No. 3 gelatin capsule. This composition may be administered orally.

DESCRIPTION 1

N-(1-Acetoxyethyl)formamide

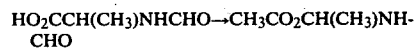

HO$_2$CCH(CH$_3$)NHCHO→CH$_3$CO$_2$CH(CH$_3$)NHCHO

N-Formyl-D,L-aniline (1.17 g, 10 mmole) and anhydrous sodium acetate (300 mg, 3.6 mmole) were dissolved in glacial acetic acid (12 ml). The resulting solution was stirred and ice-cooled while being electrolysed (two 1.5 sq.cm platinum foil electrodes placed 1 mm apart) using a current of 250–300 mA for 2 hours. The acetic acid was then removed by evaporation under reduced pressure and the residue was chromatographed on silica gel (15 g) using 1:1 ethyl acetate/petroleum ether (b.p. 60°–80°). 25 ml fractions were collected and those containing the title compound were identified using t.l.c. (silica gel; 1:1 ethyl acetate/petrol). The appropriate fractions were combined and the solvent was evaporated under reduced pressure to yield the title compound as a colourless oil (0.65 g).

DESCRIPTION 2

N-Acetoxymethyl-2-(benzyloxycarbonylamino)-acetamide

Benzyloxycarbonylglycylglycine (3.99 g, 15 mmole) was suspended in a solution of anhydrous sodium acetate (0.9 g, 11 mmole) in glacial acetic acid (75 ml). The mixture was stirred and ice-cooled while being electrolysed (two 5 sq. cm. platinum foil electrodes placed 2 mm apart) using a current of 200–250 mA for 5 hours. The acetic acid was evaporated under reduced pressure and the residue was dissolved in ethyl acetate (150 ml). The solution was washed with saturated sodium bicarbonate solution (5) ml portions, until the wash remained alkaline) and then with water (50 ml). The solution was dried (magnesium sulphate) and the solvent was evaporated under reduced pressure to yield the title compound as colourless crystals (1.85 g, 6.6 mmole).

DESCRIPTION 3

(3S, 4S)-4-Acetoxy-3-benzyloxycarbonylaminoazetidin-2-one

Benzyl 6-β-benzyloxycarbonylaminopenicillanate was converted into (3S,4S)-4-acetoxy-3-benzyloxycarbonylamino-1-(1-benxyloxycarbonyl-2-methyl-prop-1-enyl)-azetidin-2-one in 61% yield using mercuric acetate in glacial acetic acid by analogy with the process described in J. Chem. Soc., Perkin I, 1973, 32–35. The product was obtained as a colourless gum, $[\alpha]_D^{20} = -24.7°$ (c 1.1, CHCl$_3$), following purification by chromatography on silica gel using ethyl acetate/petroleum ether (b.p. 60°–80°).

The above product was converted into the title compound in 58% yield by reaction with potassium permanganate and pyridine in aqueous dimethylformamide by analogy with a process described in J. Chem. Soc., Perkin I, 1976, 447. Following chromatography on silica gel, the title compound was obtained as a colourless gum, $[\alpha]_D^{20} = -54.5°$ (c, 1.0, ethyl acetate).

DEMONSTRATION 1

Activity of Sodium 9-O-(azetidin-2'-on-4'-yl)clavulanate a. Sub-cutanvenous administration: Groups of mice were infected inter peritoneally with *Escherichia coli* JT39. At 1 and 5 hours post infection the mice were treated with amoxycillin (Amox.) or with amoxycillin and synergist. The solutions were made up in phosphate buffer.

|  | CD$_{50}$ (mg/kg × 2) |
|---|---|
| Amox. alone | >1000 |
| Amox. + 10mg/kg compound of Ex.2 | 2.4 |
| Amox. + 10mg/kg sodium clavulanate | 11.4 |
| Amox. + 2mg/kg compound of Ex.2 | 4 |
| Amox. + 2mg/kg sodium clavulanate | 21 |
| Amox. + 1mg/kg compound of Ex.2 | 6.4 |
| Amox. + 1mg/kg sodium Clavulanate | 30 | b. *Oral administration:* Groups of mice were infected inter peritoneally with *Escherichia coli* JT39. At 1, 3 and 5 hours post-infection the mice were treated with amoxycillin or with amoxycillin and synergist. The solutions were made up in phosphate buffer. The results were as follows:

|  | CD$_{50}$ (mg/kg × 3) |
|---|---|
| Amox. alone | >1000 |
| Amox. + 20mg/kg compound of Ex.2 | 6.9 |
| Amox. + 20mg/kg of sodium clavulanate | 25 | c. In vitro Activity: The following results were obtained on a standard MIC test using ampicillin and sodium 9-0-(azetidin-2'-on-4'-yl)-clavulanate:

|  | MIC (μg/ml) | | |
|---|---|---|---|
|  | Staph.aureus Russell | Klebsiella E70 | *Escherichia coli* JT39 |
| Ampicillin alone | 62 | 125 | 2000 |
| Ampicillin + 1 μg/ml synergist | 0.04 | 1.5 | 4 |
| Ampicillin + 5 μg/ml synergist | 0.01 | 0.4 | 2 |
| Synergist alone | 8 | 31.2 | 31.2 | d. Summary: The preceeding tests demonstrate that sodium 9-0-(azetidin-2'-on-4'-yl)-clavulanate is an effective synergist for penicillins such as amoxycillin against gram negative bacteria such as Escherichia and Klebsiella and gram positive bacteria such as Staphylococcus. No signs of drug toxicity were observed during the in-vivo tests.

DEMONSTRATION 2

Activity of Lithium 9-O-(1-formamidoethyl)clavulanate a. The antibacterial and synergistic activity of the title compound (referred to as "Synergist" in the Table) was determined by a conventional microliter method. The data obtained is as follows:

|  | MIC (μg/ml) | | | | | |
|---|---|---|---|---|---|---|
|  | Staph. Russell | Proteus C 889 | E. coli JT 39 | Pseudomonas Dalgleish | E coil JT 410 | Kleb. E 70 |
| Ampicillin alone | — | 1000 | 2000 | >2000 | 125 | 125 |
| Amp. + 20 μg/ml Synergist | — | — | — | 250 | 31.2 | — |
| Amp. + 5 μg/ml Synergist | ≦0.01 | 2 | 2 | 1000 | 62.5 | 3.1 |
| Amp. + 1 μg/ml Synergist | 0.04 | 4 | 31.2 | — | — | 3.1 |
| Synergist alone | 8 | 62.5 | 62.5 | >500 | 31.2 | 62.5 | b. When tested in an intra peritoneal infection due to *Escherichia coli* JT 39 in mice the title compound was found to enhance the effectiveness of amoxycillin. Dosing was sub-cutaneous and 1 and 5 hours post infection. The results were:

| Test compound | CD$_{50}$ (mg/kg) |
|---|---|
| Amoxycillin alone | >1000 × 2 |
| Amox. + 5 mg/kg Synergist | 9 × 2 |
| Cefazolin* alone | 13 × 2 |

(*Control)

DEMONSTRATION 3

Activity of 9-O-[(N-Glycyl)-2-aminoethyl]clavulanic acid

9-O-[(N-Glycyl)-2-aminoethyl]clavulanic acid was tested in a standard microliter MIC test to determine its antibacterial activity and its synergistic activity with ampicillin. The determined MIC values (μg/ml) were as follows:

|  | Staph Russell | Kleb E 70 | Proteus C 889 | E. Coli JT 39 | E. Coli JT 410 |
|---|---|---|---|---|---|
| Ampicillin alone | 250 | 500 | 2000 | 2000 | 125 |
| Amp. + | | | | | |

-continued

| | Staph Russell | Kleb E 70 | Proteus C 889 | E. Coli JT 39 | E. Coli JT 410 |
|---|---|---|---|---|---|
| 5 μg/ml of title comp. Amp. + | (0.15) | 1.5 | 2* | 8 | 62.5 |
| 1 μg/ml of title comp. | 1.25 | 6.25 | 8* | 31.2 | — |
| Title comp. alone | 8 | 62.5 | 250 | 31.2 | 62.5 |

*trailing end point

DEMONSTRATION 4

Activity of 9-O-[(3S, 4R)-3'-amino-2'-oxo-azetidin-4'-yl]clavulanic acid

9-O-[(3S, 4R)-3'-amino-2'-oxo-azetadin-4'-yl)-clavulanic acid was tested in a standard microliter MIC test to determine its antibacterial activity and its synergistic activity with ampicillin. The determined MIC values (μg/ml) were as follows:

| | Staph Russell | Kleb E 70 | Proteus C 889 | E. Coli JT 39 | E. Coli JT 410 |
|---|---|---|---|---|---|
| Ampicillin alone | 1000 | 1000 | >2000 | 1000 | 250 |
| Amp. + 5 μg/ml of title comp. | 1.25 | 6.25 | 8 | 8 | 125 |
| Amp. + 1 μg/ml of title comp. | 2.5 | 25 | 15.6 | 15.6 | — |
| Title comp. alone | 62.5 | 62.5 | 62.5 | 31.2 | 62.5 |

DEMONSTRATION 5

Activity of 9-0-[(3S, 4S)-3'-amino-2'-oxo-azetidin-4'-yl]clavulanic acid

9-O-[(3S, 4S)-3'-amino-2'-oxo-azetadin-4'-yl)-clavulanic acid was tested in a standard microliter MIC test to determine its antibacterial activity and its synergistic activity with ampicillin. The determined MIC values (μg/ml) were as follows:

| | Staph Russell | Kleb E 70 | Proteus C 889 | E. Coli JT 39 | E. Coli JT 410 |
|---|---|---|---|---|---|
| Ampicillin alone | 1000 | 1000 | >2000 | 1000 | 250 |
| Amp. + 5 μg/ml of title comp. | 0.6 | 3.12 | 8 | 4 | 125 |
| Amp. + 1 μg/ml of title comp. | 1.25 | 12.5 | 8 | 31.2 | — |
| Title comp. alone | 62.5 | 62.5 | 62.5 | 62.5 | 62.5 |

DEMONSTRATION 6

Blood levels and urinary recovery of lithium 9-O-(azetidin-2'-on-4'-yl)clavulanate Lithium 9-O-(azetidin-2'-on-4'-yl)clavulanate was administered orally to a group of eight dogs, weighing 9–12 kg, at a dosage of 5 mg/kg.

The level of the compound in the blood was measured after 0.25, 0.5, 1, 2, 4 and 6 hours. The results are shown in Table 1, with those for sodium clavulanate for comparison.

The urinary recovery of the compound over 24 hours was also measured. The results are shown in Tables 2 and 2a.

Table 1

| | Average Blood Levels (μg/ml) | | | | | |
|---|---|---|---|---|---|---|
| | Time (hr) | | | | | |
| | 0.25 | 0.5 | 1 | 2 | 4 | 6 |
| Test Compound | 1.45 | 3.64 | 4.78 | 3.79 | 0.71 | <0.2 |
| Sodium clavulanate | 0.96 | 3.11 | 2.91 | 1.68 | 0.28 | — |

Table 2

| | Urinary Recovery (mg) | | | |
|---|---|---|---|---|
| | Dog No. | | | |
| | 1 | 2 | 3 | 4 |
| 0–6 hour | 10.8 | 14.8 | 13.1 | 29.5 |
| 0–24 hour | 11.7 | 17.4 | 18.8 | 29.9 |
| % over 24 hour | 20.1 | 38.6 | 32.1 | 52.4 |

Table 2a

| | 5 | 6 | 7 | 8 |
|---|---|---|---|---|
| 0–6 hour | 18.5 | 9.2 | 9.25 | 12.15 |
| 0–24 hour | 19.6 | 10.3 | 11.1 | 12.3 |
| % over 24 hour | 37.3 | 17.2 | 19.1 | 19.5 |

I claim:

1. A compound of the formula (IV):

(IV)

or a pharmaceutically acceptable salt or in vivo hydrolyzable ester thereof wherein $R_4$ is hydrogen or $NH.CO.R_5$ wherein $R_5$ is lower alkyl, lower alkoxy, lower alkyl, aryl, aralkyl, aryloxyalkyl or aryloxy.

2. A compound according to claim 1 wherein $R_4$ is hydrogen.

3. The compound according to claim 2 in the form of the free acid.

4. The compound according to claim 2 in the form of a pharmaceutically acceptable salt.

5. A compound according to claim 1 in the form of an ester of the sub-formula (e) or (f):

(e)
$CO_2A^1$ (f)
$CO_2CHA^2A^3$ wherein $A^1$ is alkyl of 1–6 carbon atoms unsubstituted or substituted by alkoxy or acyloxy of 1–7 carbon atoms; $A^2$ is alkenyl of up to 5 carbon atoms or phenyl unsubstituted or substituted by fluorine, chlorine, bromine, nitro or alkyl or alkoxyl of up to 4 carbon atoms; and $A^3$ is hydrogen, alkyl of up to 4 carbon atoms or phenyl unsubstituted or substituted by fluorine, chlorine, bromine, nitro or alkyl or alkoxyl of up to 4 carbon atoms.

6. A compound according to claim 1 in the form of an ester of the sub-formulae (e) or (f):

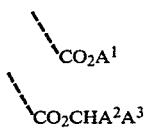

wherein $A^1$ is alkyl of 1 to 6 carbon atoms unsubstituted or substituted by alkoxyl or acyloxy of 1–7 carbon atoms; $A^2$ is alkenyl of up to 5 carbon atoms or phenyl unsubstituted or substituted by fluorine, chlorine, bromine, nitro or alkyl or alkoxyl of up to 4 carbon atoms; $A^3$ is hydrogen, alkyl of up to 4 carbon atoms or phenyl unsubstituted or substituted by fluorine, chlorine, bromine, nitro or alkyl or alkoxyl of up to 4 carbon atoms.

7. The compound according to claim 2 in the form of the lithium salt.

8. The compound according to claim 2 in the form of the sodium salt.

9. The compound according to claim 2 in the form of the potassium salt.

10. The compound according to claim 2 in the form of the calcium salt.

11. The compound according to claim 2 in the form of the magnesium salt.

12. The compound according to claim 2 in the form of the t-butylamine salt.

13. The compound according to claim 1 which is benzyl 9-O-(azetidin-2′-on-4′-yl)clavulanate.

14. The compound according to claim 1 which is benzyl 9-O-[3′-(S)-phenoxyacetamido-2′-oxoazetidin-4′-(S)-yl]clavulanate.

15. The compound according to claim 1 which is benzyl 9-O-[3′-(S)-phenoxyacetamido-2′-oxoazetidin-4′-(R)-yl]clavulanate.

16. The compound according to claim 1 which is benzyl 9-O-[(3S,4S)-2′-oxo-3′-benzyloxycarbonylaminoazetidin-4′-yl]clavulanate.

17. The compound according to claim 1 which is benzyl 9-O-[(3S,4R)-2′-oxo-3′-benzyloxycarbonylaminoazetidin-4′-yl]clavulanate.

18. The compound according to claim 1 which is benzyl 9-O-(2′-oxo-1′-benzyloxycarbonylmethylazetidin-4′-yl)clavulanate.

19. The compound according to claim 1 which is dilithium 9-O-(2′-oxo-1′-carboxymethylazetidin-4′-yl)clavulanate.

20. The compound according to claim 1 which is sodium 9-O-[(3S,4R)-3′-phenoxyacetamido-2′-oxoazetidin-4′-yl]clavulanate.

21. The compound according to claim 1 which is sodium 9-O-[(3S,4S)-3′-penoxyacetamido-2′-oxoazetidin-4′-yl]clavulanate.

22. The compound according to claim 1 which is N,N-dicyclohexylammonium 9-O-(2′-oxoazetidin-4′-yl)clavulanate.

23. The compound according to claim 1 which is pivaloyloxymethyl 9-O-(2′-oxoazetidin-4′-yl) clavulanate.

24. The compound according to claim 1 which is methyl 9-O-(2′-oxoazetidin-4′-yl) clavulate.

25. A pharmaceutical composition useful for treating bacterial infections in humans and animals and for effecting β-lactamase inhibition in humans and animals which comprises administering to a human or animal in need thereof, an antibacterially effective amount or a β-lactamase inhibitory amount of a compound of the formula (IV):

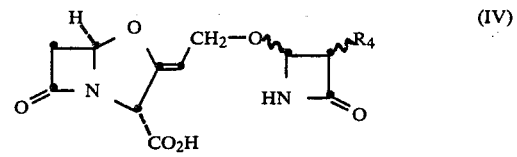

or a pharmaceutically acceptable salt or in vivo hydrolyzable ester thereof wherein $R_4$ is hydrogen or $NH.CO.R_5$, wherein $R_5$ is lower alkyl, lower alkoxy, lower alkyl, aryl, aralkyl, aryloxyalkyl or aryloxy, in combination with a pharmaceutically acceptable carrier.

26. A composition according to claim 25 wherein $R_4$ is hydrogen.

27. A composition according to claim 26 wherein the compound is in the form of the free acid.

28. A composition according to claim 26 wherein the compound is in the form of a pharmaceutically acceptable salt.

29. A composition according to claim 28 wherein the compound is in the form of the lithium salt.

30. A composition according to claim 28 wherein the compound is in the form of the sodium salt.

31. A composition according to claim 28 wherein the compound is in the form of the potassium salt.

32. A composition according to claim 28 wherein the compound is in the form of the calcium salt.

33. A composition according to claim 28 wherein the compound is in the form of the magnesium salt.

34. A composition according to claim 28 wherein the compound is in the form of the t-butylamine salt.

35. A composition according to claim 25 wherein the compound is in the form of an ester of the sub-formula (e) or (f):

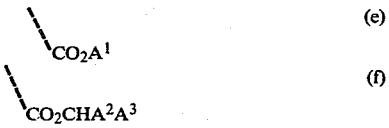

wherein $A^1$ is alkyl of 1-6 carbon atoms unsubstituted or substituted by alkoxy or acyloxy of 1-7 carbon atoms; $A^2$ is alkenyl of up to 5 carbon atoms or phenyl unsubstituted or substituted by fluorine, chlorine, bromine, nitro or alkyl or alkoxyl of up to 4 carbon atoms; and $A^3$ is hydrogen, alkyl of up to 4 carbon atoms or phenyl unsubstituted or substituted by fluorine, chlorine, bromine, nitro or alkyl or alkoxyl of up to 4 carbon atoms.

36. A composition according to claim 35 wherein the compound is in the form of an ester of the sub-formula (e) or (f):

wherein $A^1$ is alkyl of 1 to 6 carbon atoms unsubstituted or substituted by alkoxyl or acyloxy of 1–7 carbon atoms; $A^2$ is alkenyl of up to 5 carbon atoms or phenyl unsubstituted or substituted by fluorine, chlorine, bromine, nitro or alkyl or alkoxyl, alkyl of up to 4 carbon atoms or phenyl unsubstituted or substituted by fluorine, chlorine, bromine, nitro or alkyl or alkoxyl of up to 4 carbon atoms.

37. A composition according to claim 25 in oral administration form.

38. A composition according to claim 25 in parenteral administration form.

39. A composition according to claim 25 in topical application form.

40. A composition according to claim 25 wherein the compound is benzyl 9-O-azetidin-2'-on-4'-yl)clavulanate.

41. A composition according to claim 25 wherein the compound is benzyl 9-O-[3'-(S)-phenoxyacetamido-2'-oxoazetidin-4'-(S)-yl]clavulanate.

42. A composition according to claim 25 wherein the compound is benzyl 9-O-[3'-(S)-phenoxyacetamido-2'-oxoazetidin-4'-R)-yl]clavulanate.

43. A composition according to claim 25 wherein the compound is benzyl 9-O-[(3S,4S)-2'-oxo-3'-benzyloxycarbonylaminoazetidin-4'-yl]clavulanate.

44. A composition according to claim 25 wherein the compound is benzyl 9-O-[(3S,4R)-2'-oxo-3'-benzyloxycarbonylaminoazetidin-4'-yl[clavulanate.

45. A composition according to claim 25 wherein the compound is benzyl 9-O-(2'-oxo-1'-benzyloxycarbonylmethylazetidin-4'-yl)clavulanate.

46. A composition according to claim 25 wherein the compound is dilithium 9-O-(2'-oxo-1'-carboxymethylazetidin-4'-yl)clavulanate.

47. A composition according to claim 25 wherein the compound is sodium 9-O-[(3S,4R)-3'-phenoxyacetamido-2'-oxoazetidin-4'-yl]clavulanate.

48. A composition according to claim 25 wherein the compound is sodium 9-O-[(3S,4S)-3'-phenoxyacetamido-2'-oxoazetidin-4'-yl]clavulanate.

49. A composition according to claim 25 wherein the compound is N,N-dicyclohexylammonium 9-O-(2'-oxoazetidin-4'-yl) clavulanate.

50. A composition according to claim 25 wherein the compound is pivaloyloxymethyl 9-O-(2'-oxoazetidin-4'-yl) clavulanate.

51. A composition according to claim 25 wherein the compound is methyl 9-O-(2'-oxoazetidin-4'-yl) clavulanate.

52. A method of treating bacterial infections in humans and animals which comprises administering to a human or animal in need thereof, an antibacterially effective amount of a compound of the formula (IV):

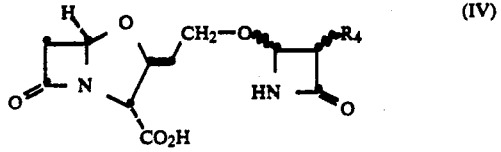

(IV)

or a pharmaceutically acceptable salt or in vivo hydrolyzable ester thereof wherein R4 is hydrogen or NH.CO.R5, wherein R5 is lower alkyl, lower alkoxy, lower alky, aryl, aralkyl, aryloxyalkyl or aryloxy.

53. A method according to claim 52 wherein R4 is hydrogen.

54. A method according to claim 53 wherein the compound is in the form of the free acid.

55. A method according to claim 53 wherein the compound is in the form of a pharmaceutically acceptable salt.

56. A method according to claim 55 wherein the compound is in the form of the lithium salt.

57. A method according to claim 55 wherein the compound is in the form of the sodium salt.

58. A method according to claim 55 wherein the compound is in the form of the potassium salt.

59. A method according to claim 55 wherein the compound is in the form of the calcium salt.

60. A method according to claim 55 wherein the compound is in the form of the magnesium salt.

61. A method according to claim 55 wherein the compound is in the form of the t-butylamine salt.

62. A method according to claim 52 wherein the compound is in the form of an ester of the sub-formula (e) or (f):

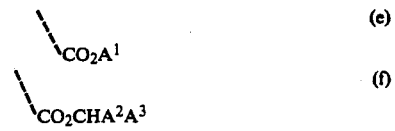

wherein $A^1$ is alkyl of 1-6 carbon atoms unsubstituted or substituted by alkoxy or acyloxy of 1-7 carbon atoms; $A^2$ is alkenyl of up to 5 carbon atoms or phenyl unsubstituted or substituted by fluorine, chlorine, bromine, nitro or alkyl or alkoxyl of up to 4 carbon atoms; and $A^3$ is hydrogen, alkyl of up to 4 carbon atoms or phenyl unsubstituted or substituted by fluorine, chlorine, bromine, nitro or alkyl or alkoxyl of up to 4 carbon atoms.

63. A method according to claim 62 wherein the compound is in the form of an ester of the sub-formula (e) or (f):

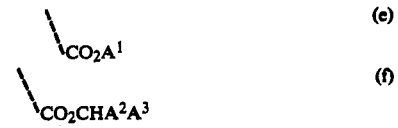

wherein $A^1$ is alkyl of 1 to 6 carbon atoms unsubstituted or substituted by alkoxyl or acyloxy of 1-7 carbon atoms; $A^2$ is alkenyl of up to 5 carbon atoms or phenyl unsubstituted or substituted by fluorine, chlorine, bromine, nitro or alkyl or alkoxyl, alkyl of up to 4 carbon atoms or phenyl unsubstituted or substituted by fluorine, chlorine, bromine, nitro or alkyl or alkoxyl of up to 4 carbon atoms.

64. A method according to claim 52 wherein the administration is oral.

65. A method according to claim 52 wherein the administration is parenteral.

66. A method according to claim 52 wherein the administration is by topical application.

67. A method according to claim 52 wherein the compound is benzyl 9-O-(azetidin-2'-on-4'-yl) clavulanate.

68. A method according to claim 52 wherein the compound is benzyl 9-O-[3'-(S)-phenoxyacetamido-2'-oxoazetidin-4'-(S)-yl]clavulanate.

69. A method according to claim 52 wherein the compound is benzyl 9-O-[3'-(S)-phenoxyacetamido-2'-oxoazetidin-4'-(R)-yl]clavulanate.

70. A method according to claim 52 wherein the compound is benzyl 9-O-[(3S,4S)-2'-oxo-3'-benzyloxycarbonylaminoazetidin-4'-yl]clavulanate.

71. A method according to claim 52 wherein the compound is benzyl 9-O-[(3S,4R)-2'-oxo-3'-benzyloxycarbonylaminoazetidin-4'-yl]clavulanate.

72. A method according to claim 52 wherein the compound is benzyl 9-O-(2'-oxo-1'-benzyloxycarbonylmethylazetidin-4'-yl)clavulanate.

73. A method according to claim 52 wherein the compound is dilithium 9-O-(2'-oxo-1'-carboxymethylazetidin-4'-yl)clavulanate.

74. A method according to claim 52 wherein the compound is sodium 9-O-[(3S,4R)-3'-phenoxyacetamido-2'-oxoazetidin-4'-yl[clavulanate.

75. A method according to claim 52 wherein the compound is sodium 9-O-[(3S,4S)-3'-phenoxyacetamido-2'-oxoazetidin-4'-yl]clavulanate.

76. A method according to claim 52 wherein the compound is N,N-dicyclohexylammonium 9-O-(2'-oxoazetidin-4'-yl)clavulanate.

77. A method according to claim 52 wherein the compound is pivaloyloxymethyl 9-O-(2'-oxoazetidin-4'-yl) clavulanate.

78. A method according to claim 52 wherein the compound is methyl 9-O-(2'-oxoazetidin-4'-yl) clavulanate.

* * * * *